United States Patent [19]
Kriesel

[11] Patent Number: 5,993,421
[45] Date of Patent: Nov. 30, 1999

[54] MEDICAMENT DISPENSER

[75] Inventor: Marshall S Kriesel, St. Paul, Minn.

[73] Assignee: Science Incorporated, Bloomington, Minn.

[21] Appl. No.: 08/992,126

[22] Filed: Dec. 16, 1997

Related U.S. Application Data

[63] Continuation-in-part of application No. 08/473,650, Jun. 6, 1995, Pat. No. 5,743,879, which is a continuation-in-part of application No. 08/349,496, Dec. 2, 1994, abandoned.

[51] Int. Cl.⁶ ................................................ A61M 37/00
[52] U.S. Cl. .................................. 604/132; 128/DIG. 12; 604/151
[58] Field of Search .................................... 604/131, 132, 604/184, 185, 140, 141, 157, 135, 151; 128/DIG. 12

[56] References Cited

U.S. PATENT DOCUMENTS

| | | | |
|---|---|---|---|
| 4,474,575 | 10/1984 | Eckenhoff et al. | 604/131 |
| 4,968,301 | 11/1990 | DiPalma et al. | 604/132 |
| 5,779,676 | 7/1998 | Kriesel et al. | 604/132 |
| 5,807,335 | 9/1998 | Kriesel et al. | 604/131 |

*Primary Examiner*—John D. Yasko
*Attorney, Agent, or Firm*—James E. Brunton

[57] ABSTRACT

A compact fluid dispenser for use in controllably dispensing fluid medicaments and a cooperating reservoir fill assembly for controllably filling the fluid reservoir of the fluid dispenser. The fluid dispenser component includes a novel stored energy source in the form of an expandable, elastomeric member of unique construction that provides the force necessary to continuously and substantially uniformly expel fluid from the reservoir of the dispenser component. The fluid dispenser component further includes a fluid flow control assembly that filters and precisely controls the flow of the medicament solution from the reservoir of the dispenser container.

33 Claims, 15 Drawing Sheets

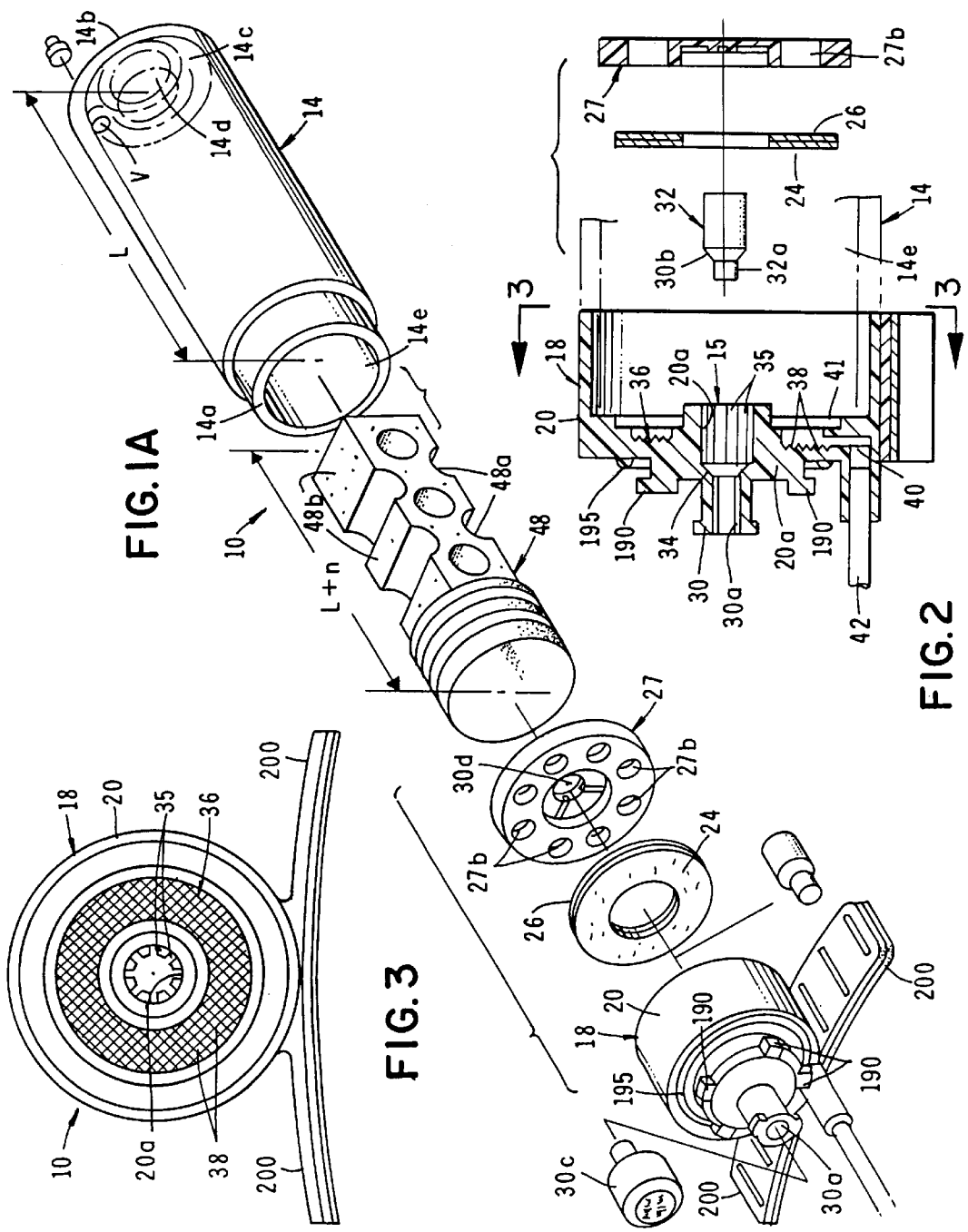

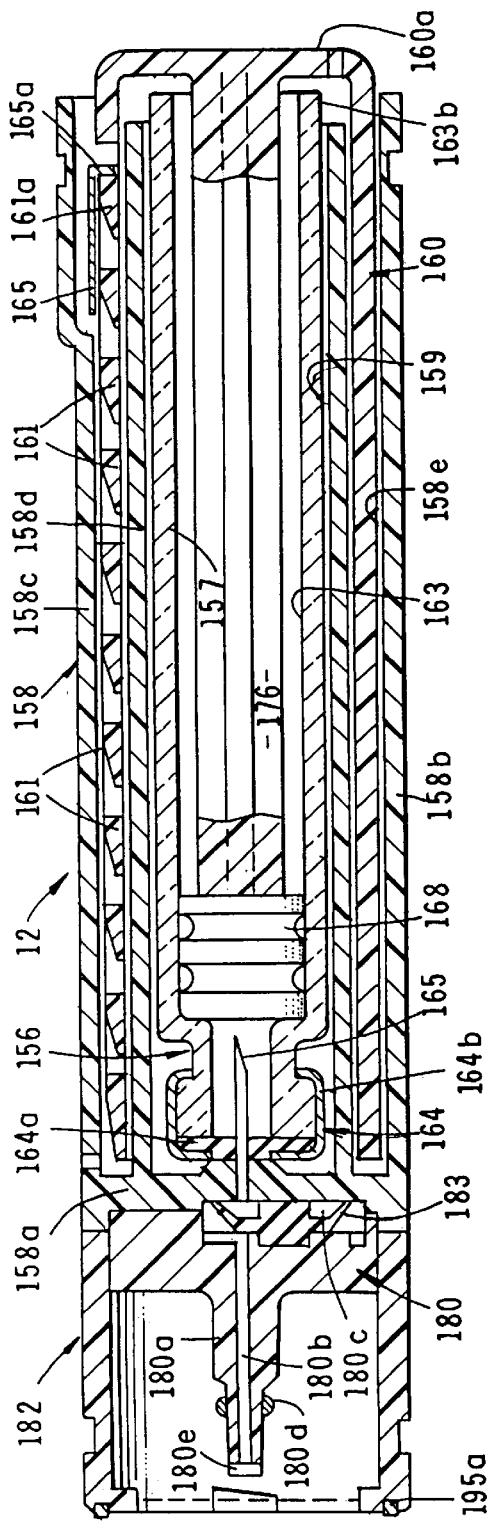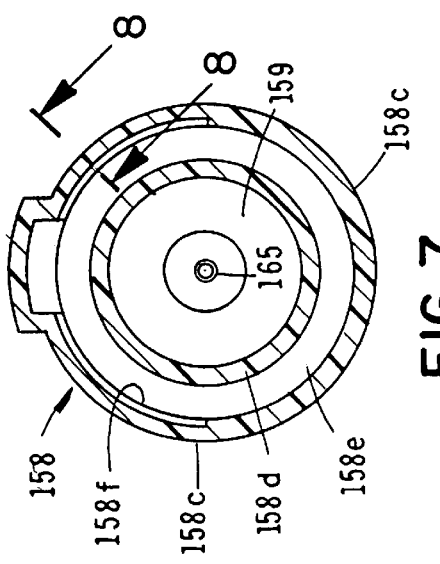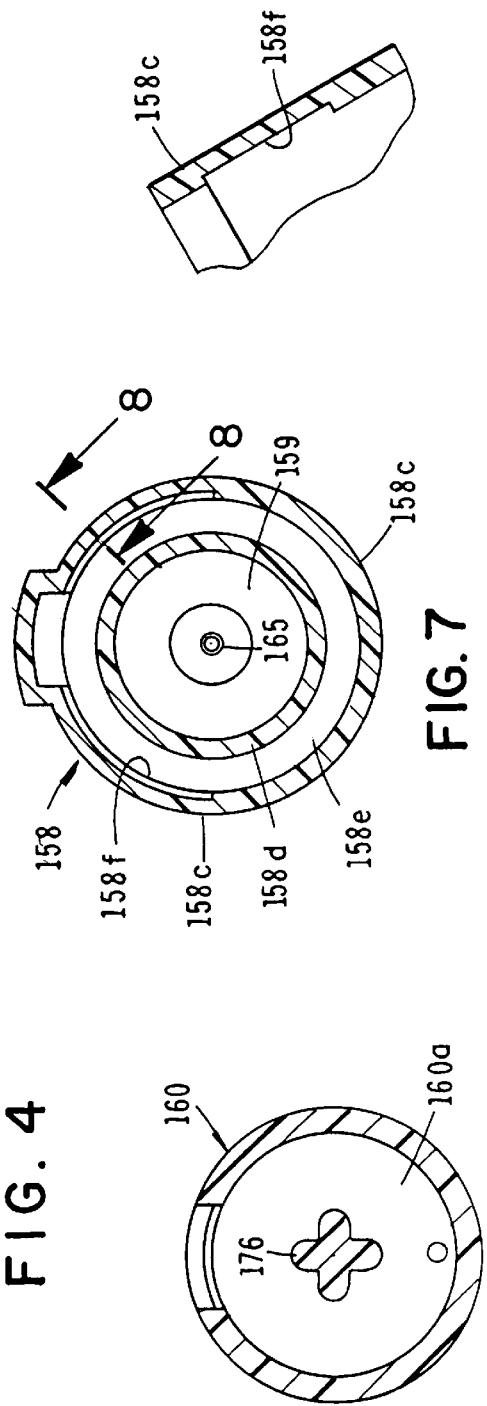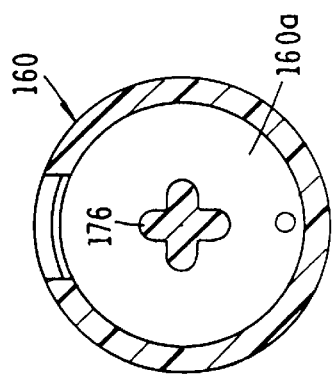

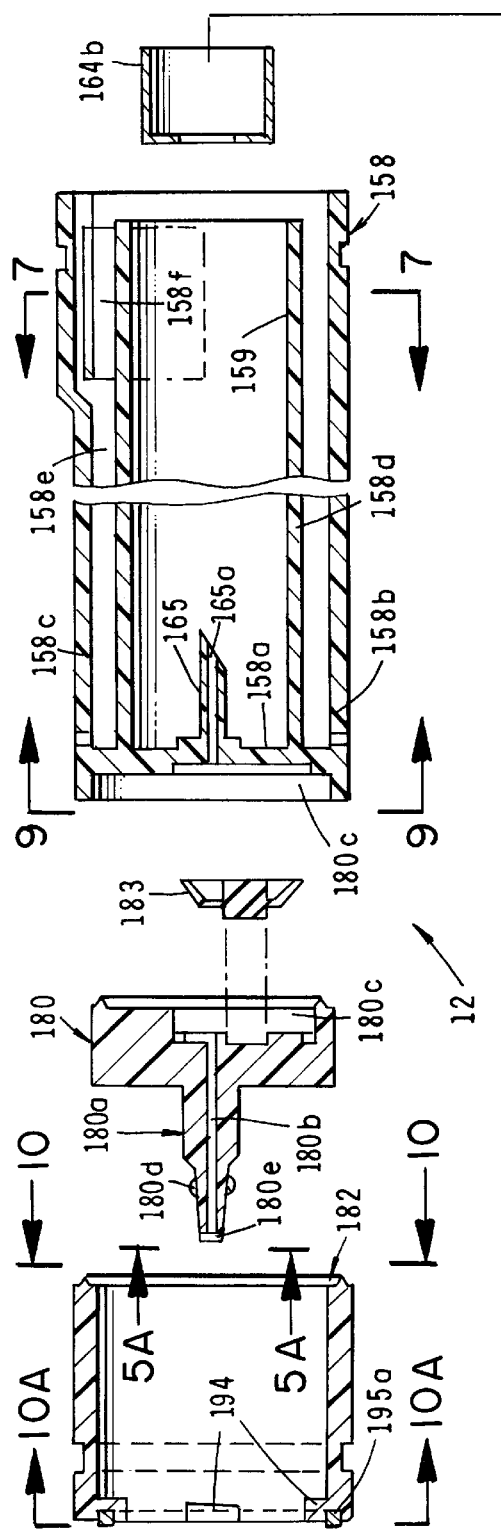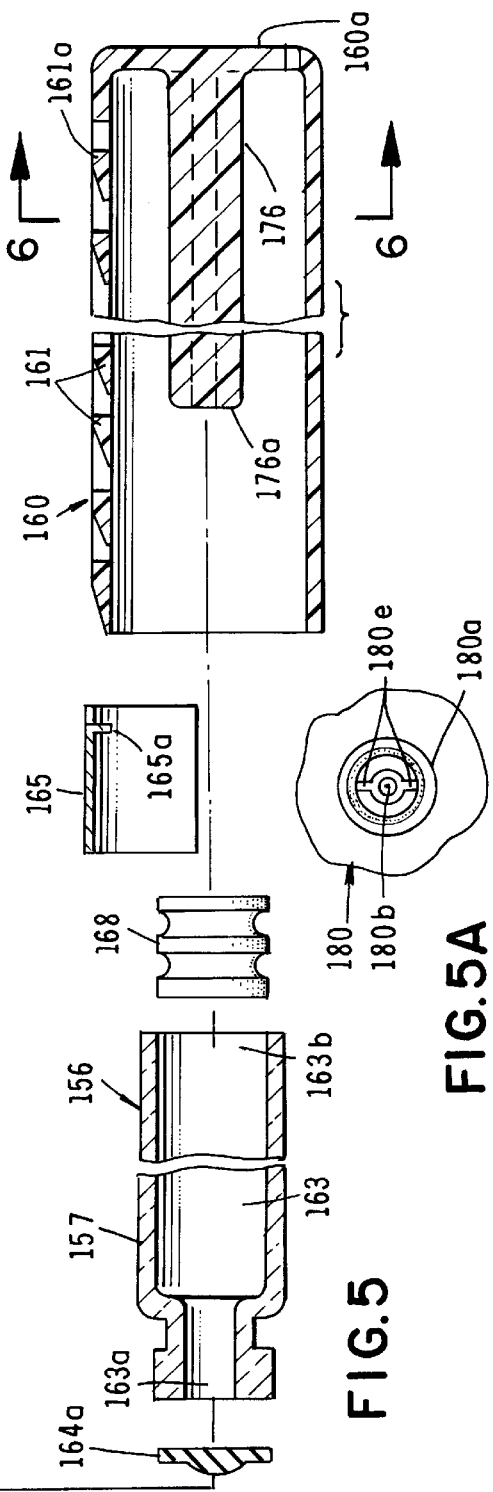
FIG.5
FIG.5A

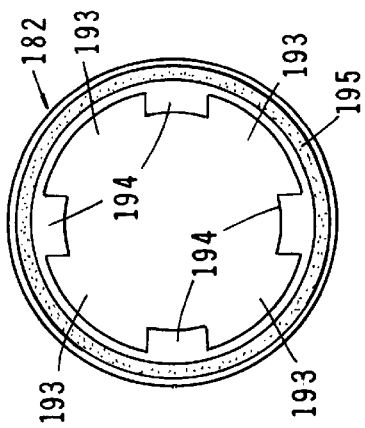
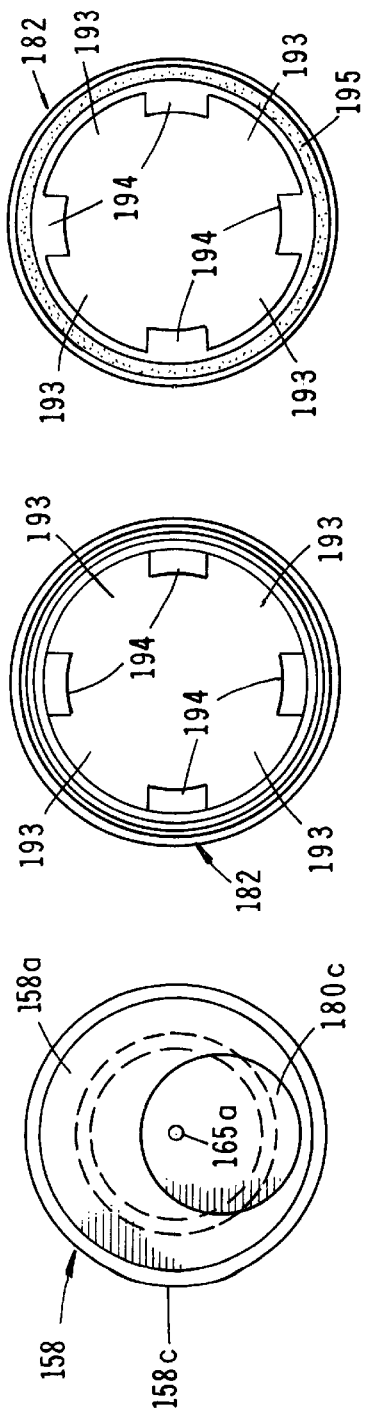
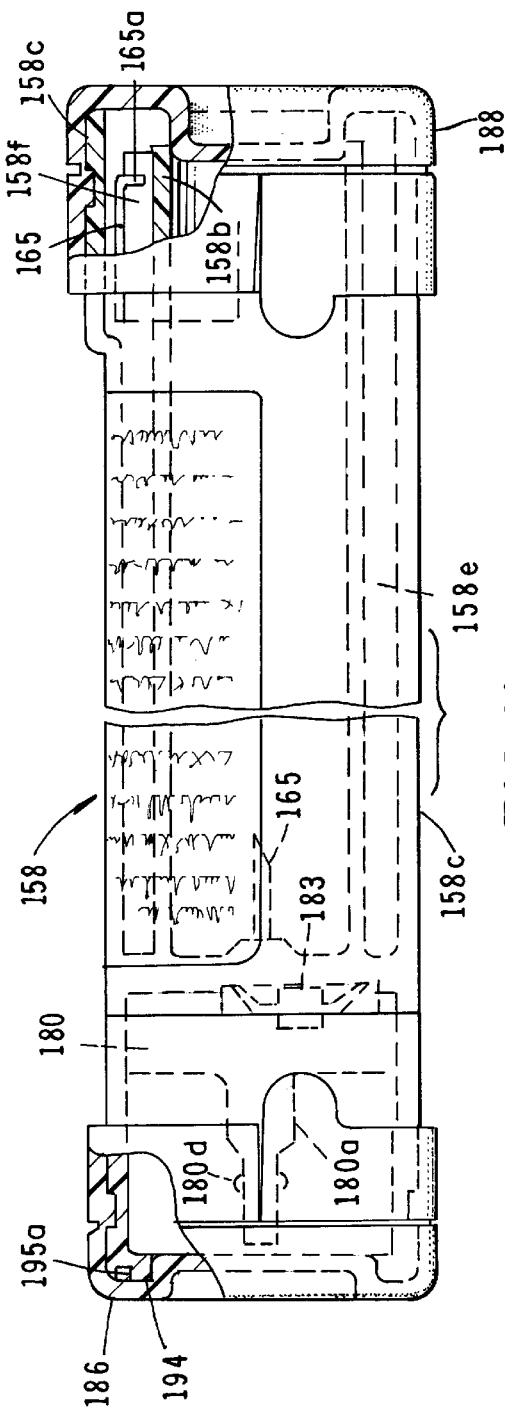

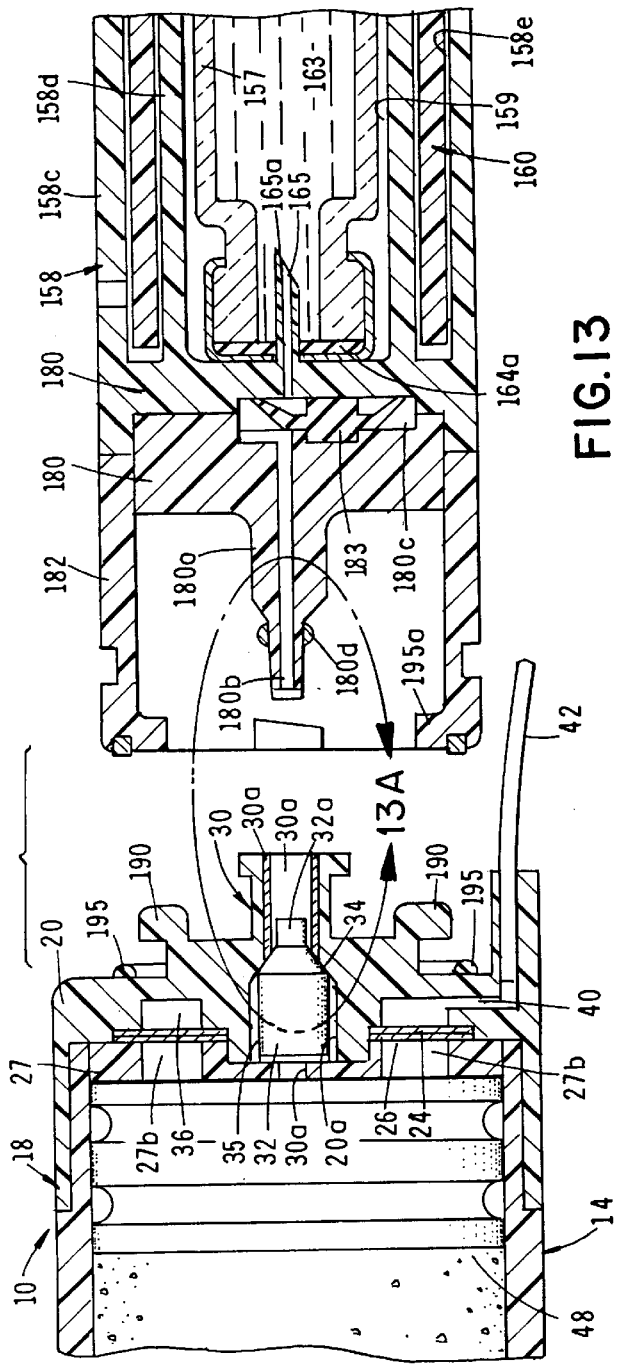
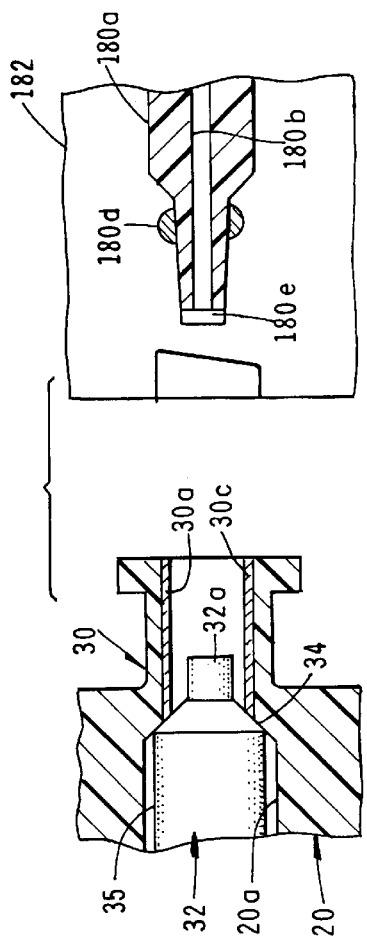
FIG. 13
FIG. 13A

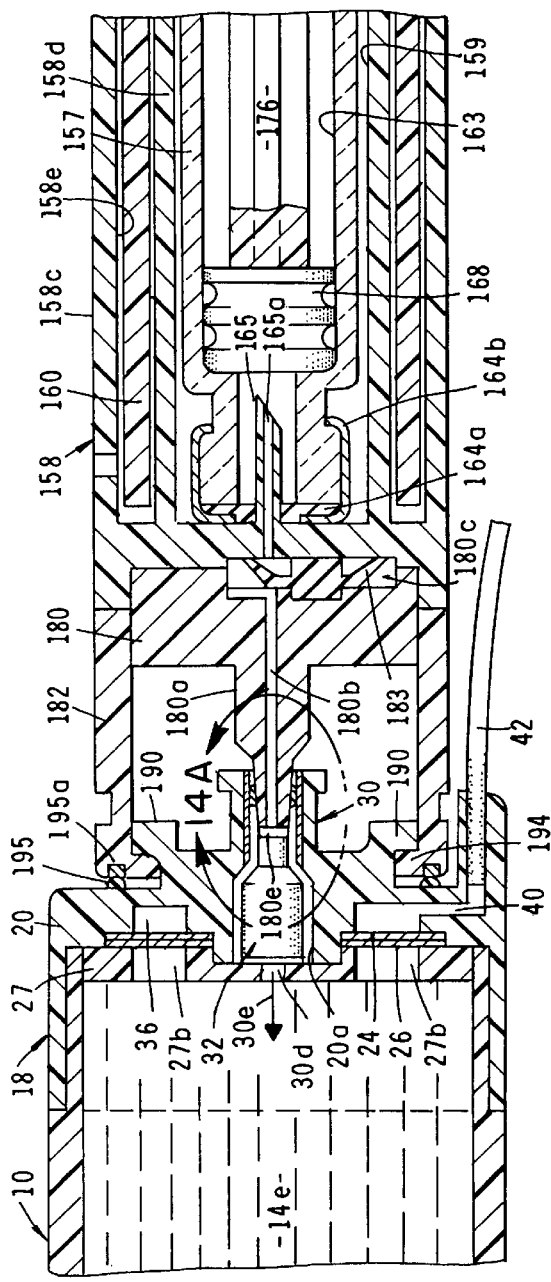
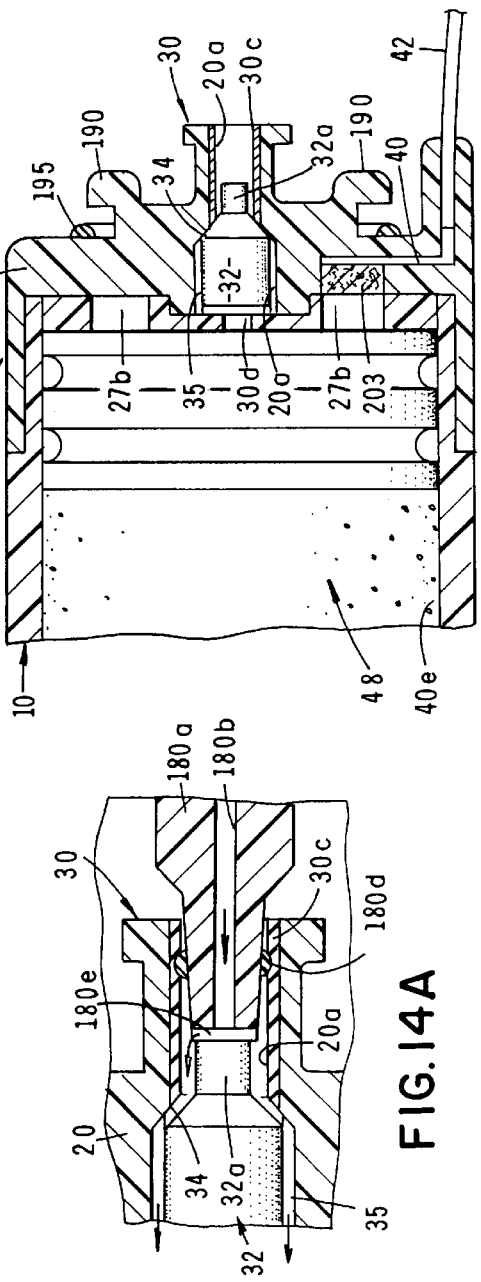
FIG. 14
FIG. 14A
FIG. 15

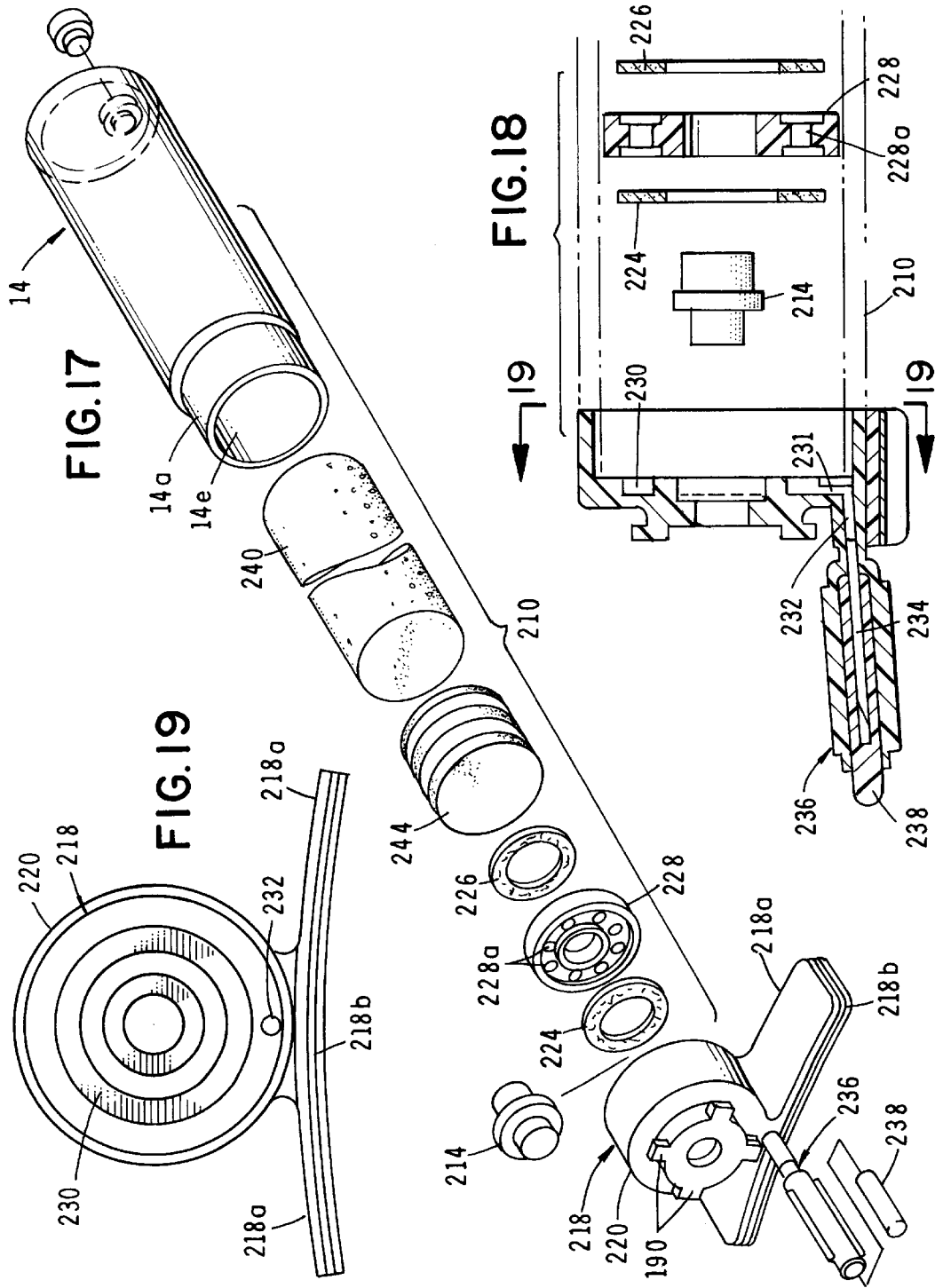

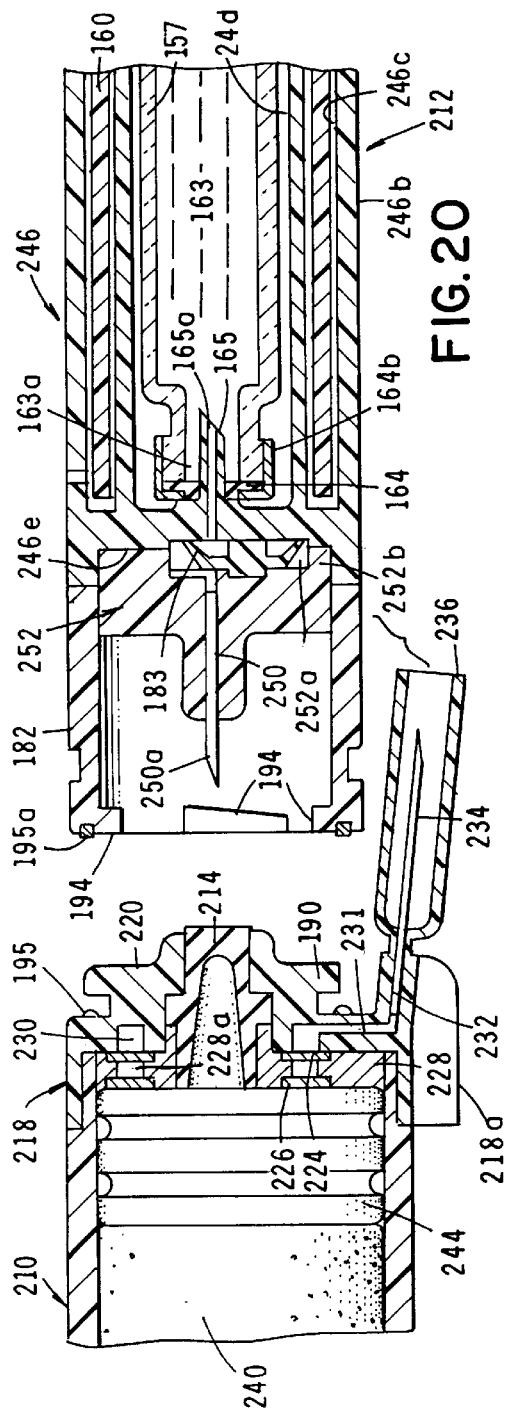

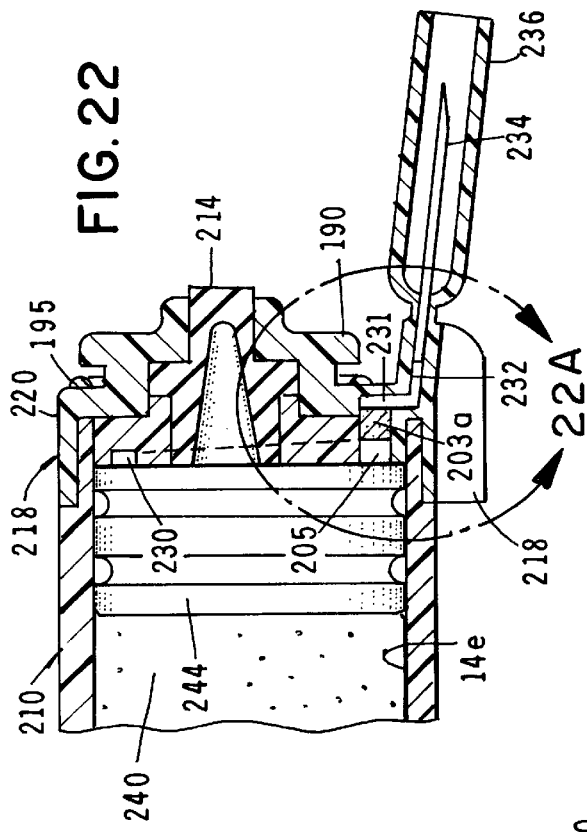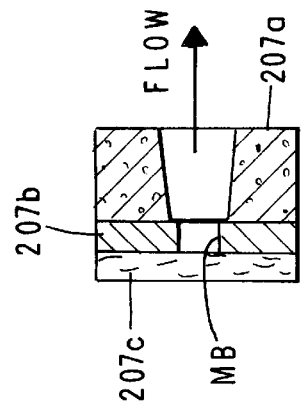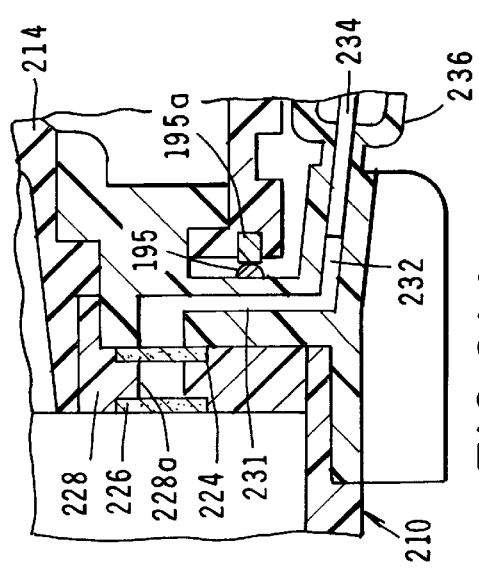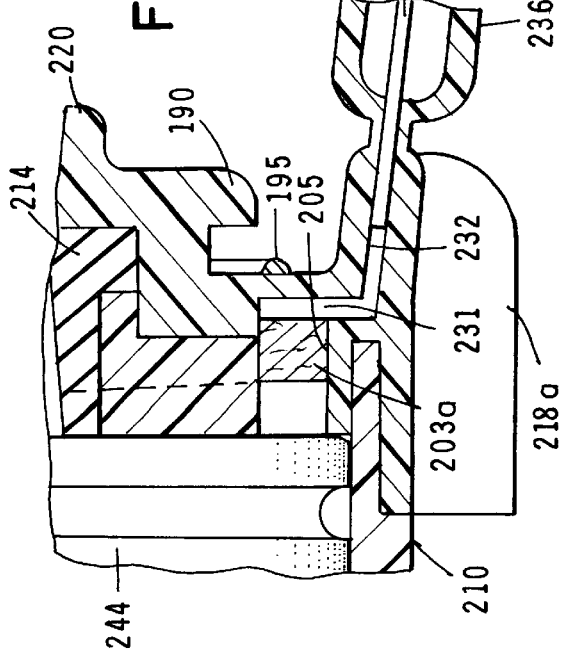

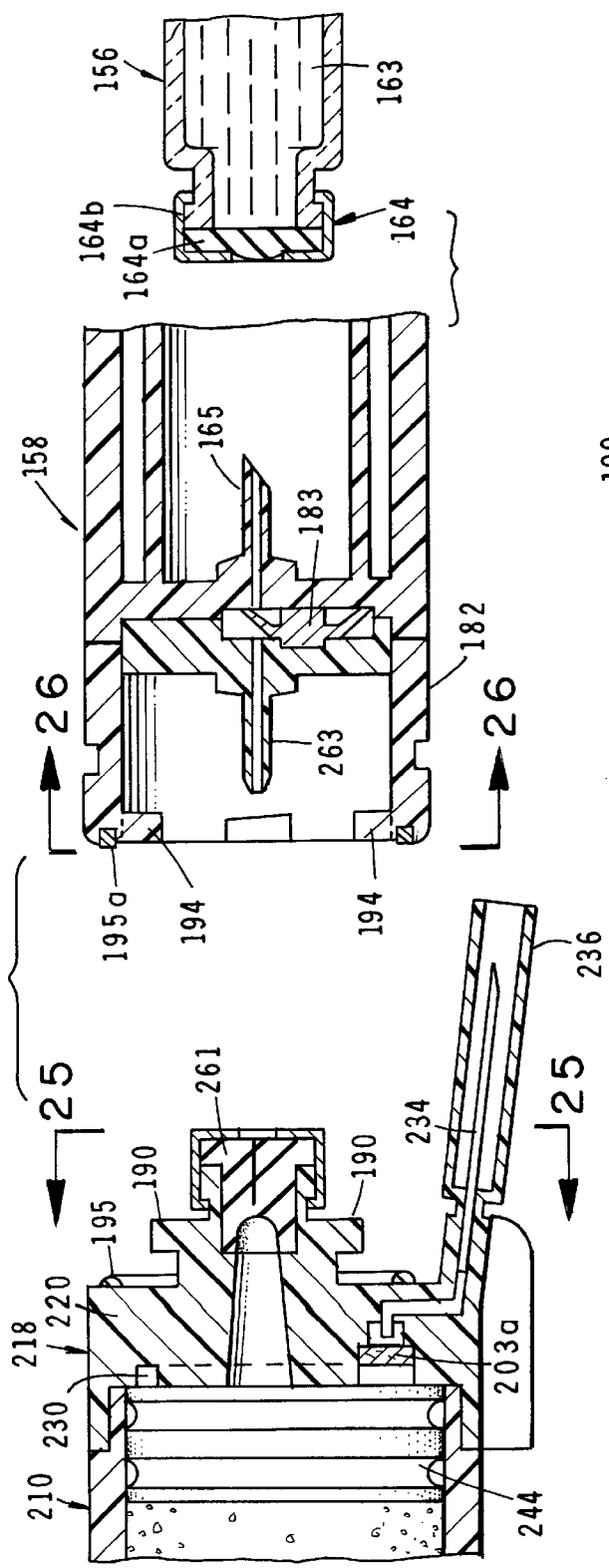
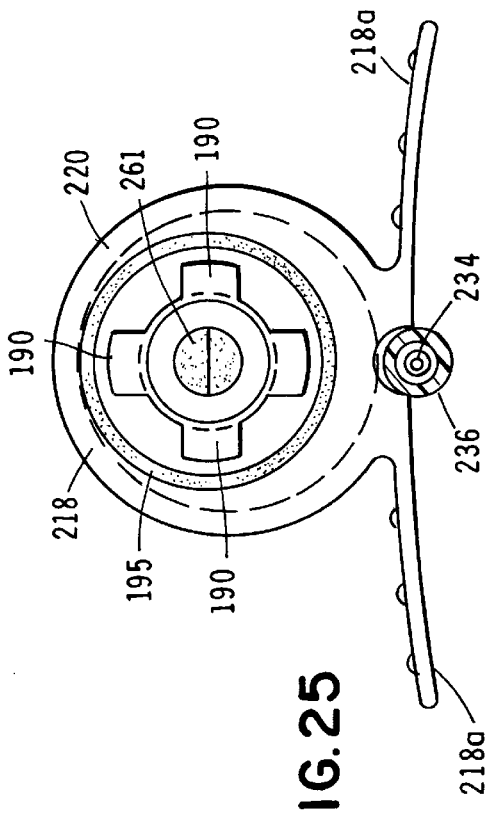
FIG. 23
FIG. 25

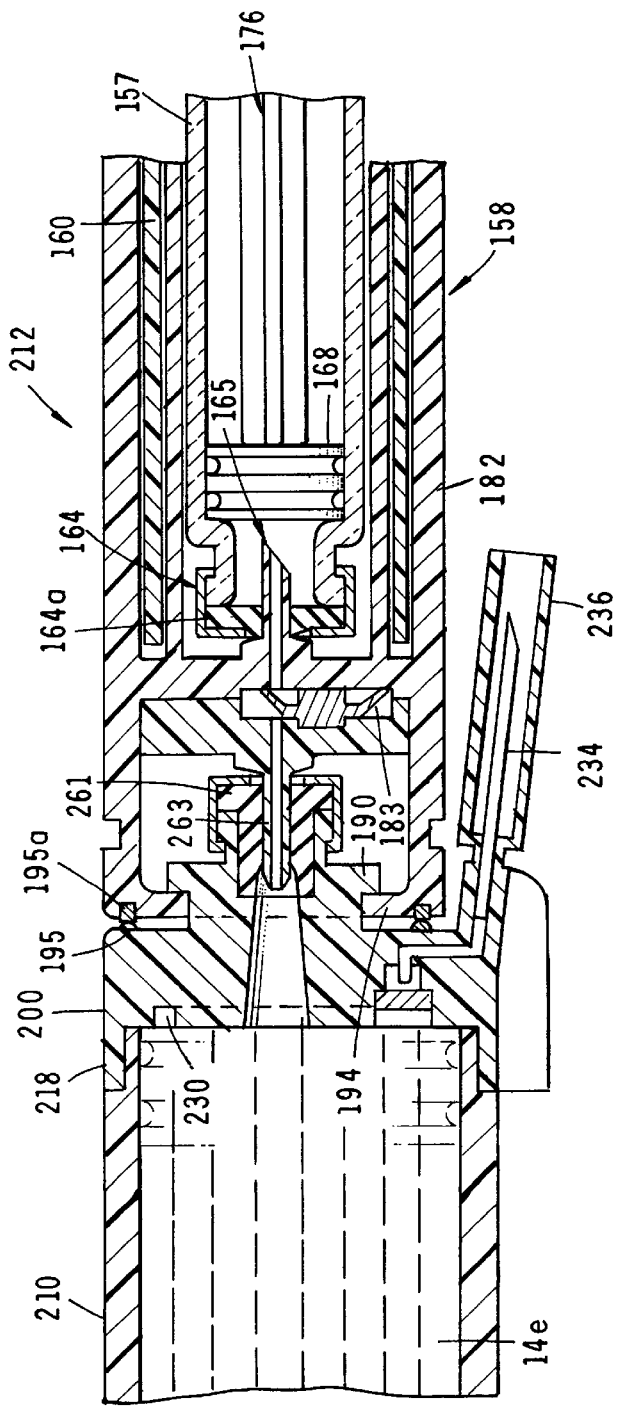
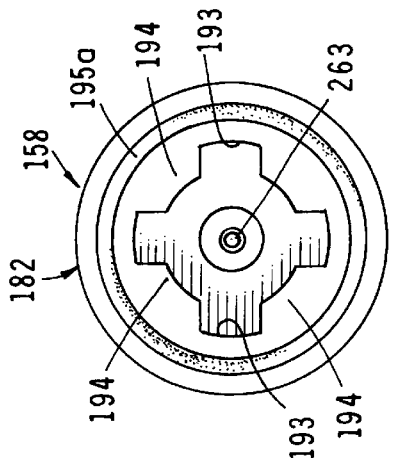
FIG. 24
FIG. 26

MEDICAMENT DISPENSER

BACKGROUND OF THE INVENTION

This is a Continuation-In-Part of application of U.S. Ser. No. 08/473,650 filed Jun. 6, 1995 which has now issued into U.S. Pat. No. 5,743,879; which is a Continuation-In-Part of U.S. Ser. No. 08/349,496 filed Dec. 2, 1994 and now abandoned.

FIELD OF THE INVENTION

The present invention relates generally to fluid medicament dispensers. More particularly, the invention concerns a dispenser for use in controllably dispensing a liquid medicament and a cooperating medicament fill assembly for filling the reservoir of the dispenser.

DISCUSSION OF THE PRIOR ART

Traditionally, conventional syringes are used to inject many beneficial agent solutions such as insulin. In accordance with conventional procedures, the prescribed dose is first drawn into the syringe and a visual check is made to make certain that the correct amount of insulin is present in the syringe. Next, air is expelled from the syringe and the dose is injected manually.

These conventional procedures have numerous drawbacks including adverse reaction caused by the bolus injection of drugs by hand via a syringe. In the majority of cases, the adverse reactions are not due to the drug itself, but rather are due to an improper dosing rate of injection of the drug. In many therapeutic situations, the contents of a syringe should be delivered over a number of minutes or hours. However, in clinical practice, this rarely occurs due to time pressure on the medical professional staff who must operate the syringe manually.

Because diabetics generally require regular and repeated injections of insulin, the use of multiple injections from self-delivering devices, such as conventional syringes, is cumbersome, time consuming, and dangerous if not properly performed. In addition, the process of sticking one's self and infusing the liquid medicament can be extremely unpleasant for the medically untrained. For this reason, several types of dispensing devices have been suggested for automatically dispensing a predetermined quantity of a liquid medicament such as insulin from a multi-does container. Exemplary of such devices are those described in European Patent Application No. 37696 and in U.S. Pat. No. 4,592,745 issued to Rex, et al. Both of the aforementioned devices dispense a predetermined quantity of liquid from a liquid reservoir or container and both include mechanical operating mechanisms for expelling the fluid from the reservoir.

The Rex, et al device comprises an elongated body formed from two separable sections one of which contains an operating mechanism and the other of which contains a prefilled cartridge. The operating mechanism of the device mechanically advances an axially movable piston rod which, in turn, drives a piston plug located inside the cartridge so as to expel fluid from the device via a needle located at the bottom end of the body. The piston rod advances in successive axial steps of fixed length through rotation of a rotatable piston rod nut. The piston rod nut is driven by a rotatable worm, which is rotated by the advancing axial movement of a pressure device located at the top of the elongated body.

The EPO application discloses a dispensing device somewhat similar to the Rex, et al. device, but embodies an operating mechanism that comprises a pawl which permits relative movement of a ratchet-toothed member in a substantially rectilinear arrangement. As in the Rex, et al. device, the operating mechanism drives the plunger of a medicament vial to expel fluid therefrom.

U.S. Pat. No. 4,813,937 issued to Vaillancourt discloses an infusion system in which the inflow of fluid into the device causes an elastomeric member attached to a piston to be moved so as to stretch the elastomeric member. The thusly tensioned elastomeric member provides the source of energy to expel the fluid from the device when the outlet tubing of the system is opened. However, as is clear from a study of the Vaillancourt patent, the device disclosed therein operates in a substantially different manner than the device of the present invention.

Electrically operated syringe pumps are also well known, however, they are typically of considerable complexity and are designed to inject very small doses of medicine with considerable accuracy over a long period, which may be up to 24 hours. Such syringe pumps do not provide the inexpensive, simple and manually operated device suitable for the slow injection of drugs over a shorter period of time, which may range from one to 15 minutes.

Many of the prior art medicament dispensing devices are of complex construction and, therefore, are often very expensive to manufacture. Additionally, such devices tend to be somewhat unreliable in use and frequently have a limited useful life. In using certain of the prior art devices, maintaining sterility has also proven to be a problem.

As will be appreciated from the discussion which follows, the apparatus of the present invention uniquely overcomes the drawbacks of the prior art by providing a novel, disposable dispenser of simple but highly reliable construction. A particularly important aspect of the apparatus of the present invention resides in the provision of a novel, self-contained energy source in the form of a constant-force spring that provides the force necessary to uniformly and precisely dispense solutions, such as insulin, from standard prefilled containers that can be conveniently loaded into the apparatus. Because of the simplicity of construction of the apparatus of the invention, and the straight-forward nature of the energy source, the apparatus can be manufactured at low cost without in any way sacrificing accuracy and reliability.

A somewhat similar medicament dispenser is disclosed in application Ser. No. 08/473,650 filed Jun. 6, 1995 and has now issued into U.S. Pat. No. 5,743,879 filed by the present inventor. Because the present application is directed toward an improvement of the invention disclosed in this application, application, Ser. No. 08/473,650 which was filed Jun. 6, 1995 and now issued into U.S. Pat. No. 5,743,879 is hereby incorporated by reference as though fully set forth herein. As will be discussed in detail hereinafter, the present invention includes a novel filling means for use with one or more of the devices disclosed in this earlier filed application to fill the fluid reservoirs of the devices.

SUMMARY OF THE INVENTION

It is an object of the present invention to provide a small, compact fluid dispenser for use in controllably dispensing fluid medicaments; hormones, such as insulin; or other diabetes related agents; antibiotics; oncolytics; analgesics, bio-pharmaceutics, other injectable therapeutics, and related diagnostic agents, and the like and a cooperating reservoir fill assembly for controllably filling the fluid reservoir of the fluid dispenser.

Another object is to provide a device of the aforementioned character which is of very simple construction and embodies a minimum number of parts.

Another object of the invention is to provide a disposable small fluid dispenser component which is compact and easy to fill using the novel reservoir fill assembly of the invention.

Another object of the invention is to provide a fluid dispenser component within which a stored energy source is provided in the form of an expandable, elastomeric member of novel construction that provides the force necessary to continuously and substantially uniformly expel fluid from the prefilled container.

Another object of the invention is to provide a fluid dispenser component of the class described which includes a fluid flow control assembly that filters and precisely controls the flow of the medicament solution from the reservoir of the dispenser container.

Another object of the invention is to provide a novel reservoir fill assembly for use in filling the fluid reservoir of the fluid dispenser which fill assembly is compact, easy to use and is of simple construction.

Another object of the invention is to provide an apparatus of the aforementioned character in which the reservoir fill assembly comprises a vial cartridge assembly that can be prefilled with a wide variety of medicinal fluids.

Another object of the present invention is to provide a reservoir fill assembly of the type described in the preceding paragraph in which the prefilled vial cartridge assembly is housed within a novel adapter assembly which is readily mateably with the fluid dispensing apparatus for controllably filling the reservoir thereof.

Another object of the invention is to provide a fluid dispenser and cooperating reservoir fill assembly of the class described which is lightweight, is easy for ambulatory patients to use, is fully disposable, and is extremely accurate so as to enable the infusion of precise doses of medicaments such as morphine over prescribed periods of time.

Another object of the invention is to provide an easy-to-use medicament dispenser and cooperating reservoir fill assembly which is extremely durable and highly reliable in use.

Another object of the invention is to provide a dispenser of the class described which includes means for attaching the device with the body or clothing of the patient.

Another object of the invention is to provide a fluid dispenser as described in the preceding paragraphs which includes transport means for easy transport and storage of both the dispenser and fill components of the invention.

BRIEF DESCRIPTION OF THE DRAWINGS

FIG. 1A is a generally perspective, exploded view of the dispensing apparatus shown in FIG. 1.

FIG. 2 is a fragmentary, cross-sectional view of the forward portion of the dispensing apparatus.

FIG. 3 is a view taken along lines 3—3 of FIG. 2.

FIG. 4 is an enlarged, side-elevational, cross-sectional view of the assembled reservoir fill assembly of the form of the invention shown in FIG. 1.

FIG. 5 is an exploded, side-elevational view of the entire reservoir fill assembly shown in FIG. 4.

FIG. 5A is an enlarged view taken along lines 5A—5A of FIG. 5.

FIG. 6 is a cross-sectional view taken along lines 6—6 of FIG. 5.

FIG. 7 is a cross-sectional view taken along lines 7—7 of FIG. 5.

FIG. 8 is a cross-sectional view taken along lines 8—8 of FIG. 7.

FIG. 9 is a cross-sectional view taken along lines 9—9 of FIG. 5.

FIG. 10 is a cross-sectional view taken along lines 10—10 of FIG. 4A.

FIG. 10A is a view taken along lines 10A-10A of FIG. 5.

FIG. 11 is a foreshortened, side-elevational view of the fully assembly reservoir fill assembly partly broken away to show internal construction.

FIG. 13 is a fragmentary, side-elevational, cross-sectional view showing the fluid dispensing apparatus in a position to be mated with the reservoir fill assembly.

FIG. 13A is an enlarged fragmentary, cross-sectional view of the area identified in FIG. 13 as 13A.

FIG. 14 is a fragmentary, side-elevational, cross-sectional view similar to FIG. 13 but showing the fluid dispensing apparatus mated with the reservoir fill assembly.

FIG. 14A is an enlarged, fragmentary, cross-sectional view of the area identified in FIG. 14 as 14A.

FIG. 15 is a fragmentary, cross-sectional view of the forward portion of an alternate embodiment of the dispensing apparatus of the invention showing another type of a fluid flow control means for controlling fluid flow from the apparatus.

FIG. 17 is a generally perspective, exploded view of the dispensing apparatus shown in FIG. 16.

FIG. 18 is a fragmentary, cross-sectional view of the forward portion of the dispensing apparatus of FIG. 17.

FIG. 19 is a view taken along lines 19—19 of FIG. 18.

FIG. 20 is a fragmentary, side-elevational, cross-sectional view showing the fluid dispensing apparatus of this latest form of the invention in a position to be mated with the reservoir fill assembly.

FIG. 21 is a fragmentary, side-elevational, cross-sectional view similar to FIG. 20 but showing the fluid dispensing apparatus mated with the reservoir fill assembly.

FIG. 21A is an enlarged, fragmentary, cross-sectional view of the area identified in FIG. 21 by the numeral 21A.

FIG. 22 is a fragmentary, cross-sectional view of the forward portion of an alternate embodiment of the dispensing apparatus of this latest form of the invention showing an alternate form of a fluid flow control means for controlling fluid flow from the apparatus.

FIG. 22A is an enlarged, fragmentary, cross-sectional view of the area identified in FIG. 22 by the numeral 22A.

FIG. 22B is an enlarged, cross-sectional view of an alternate form of flow control means which comprises a unique laser drilled wafer element.

FIG. 23 is a fragmentary, side-elevational, cross-sectional view of an alternate form of the invention showing a fluid dispensing apparatus having a slit septum in a position to be mated with the reservoir fill assembly having a blunt end cannula.

FIG. 24 is a fragmentary, side-elevational, cross-sectional view of the embodiment of FIG. 23 showing the fluid dispensing unit mated with the reservoir fill assembly.

FIG. 25 is a view taken along lines 25—25 of FIG. 23.

FIG. 26 is a view taken along lines 26—26 of FIG. 23.

DESCRIPTION OF THE INVENTION

Figure 1:
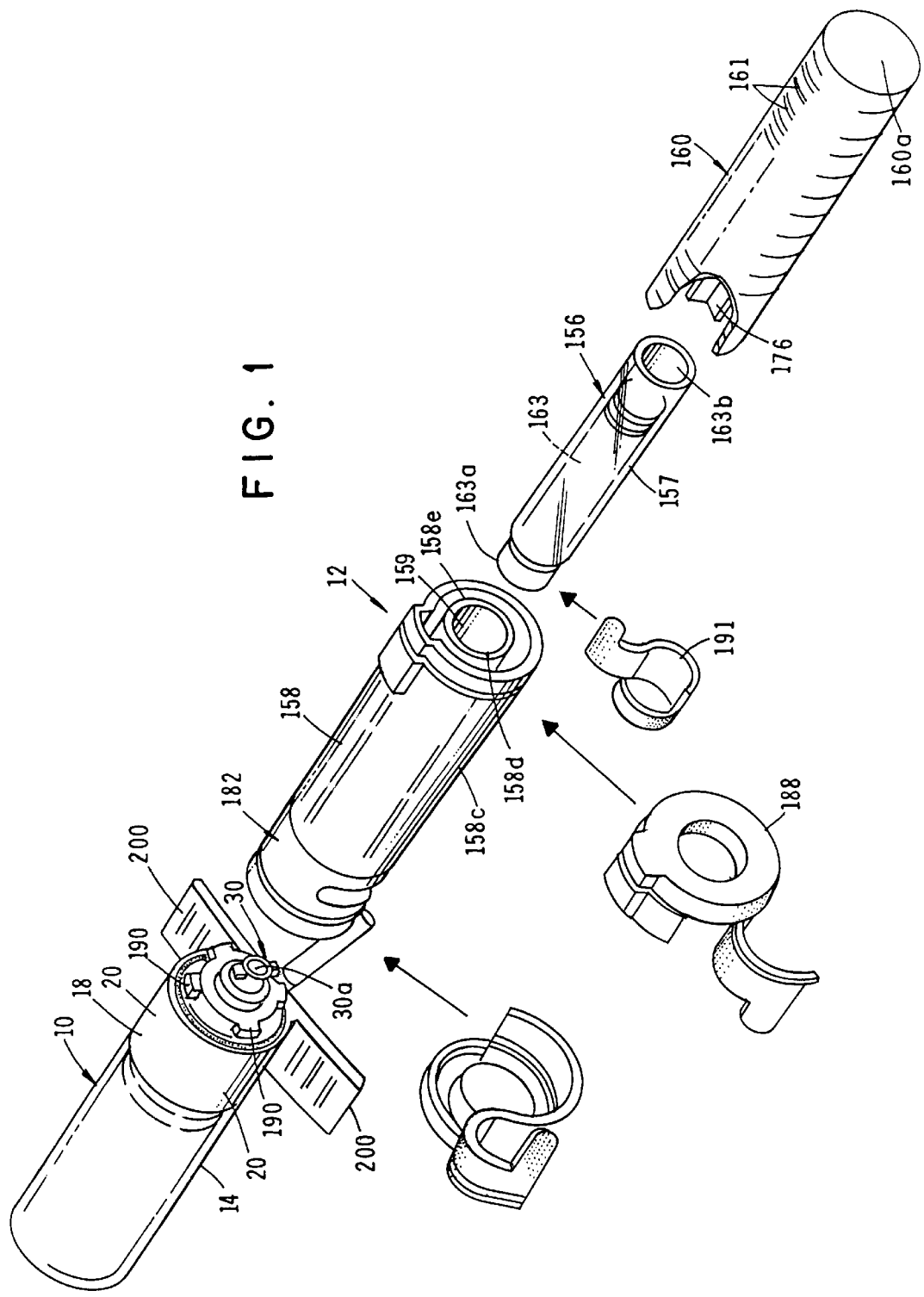
FIG. 1 is a generally perspective, exploded view of one embodiment of the fluid dispensing apparatus and reservoir fill assembly of the present invention.

Referring to the drawings and particularly to FIGS. 1 through 12, one embodiment of the dispensing apparatus of the invention is there shown and can be seen to comprise a fluid medicament dispenser and a cooperating reservoir fill assembly. In FIG. 1, the medicament dispenser is shown fully assembled and is generally designated by the numeral 10. The reservoir fill assembly, on the other hand, is shown in exploded form and is generally designated in FIG. 1 by the numeral 12. The medicament dispenser 10 is of the same general character as that described in U.S. Ser. No. 08/473,650 which application is incorporated herein by reference.

As best seen in FIGS. 1A, 2, and 3, the medicament dispenser 10 of the present form of the invention comprises a housing assembly including a housing or container 14, having a first open end 14a and a closed end 14b. End 14b is closed by an end wall 14c having a centrally disposed socket like portion 14d and a vent "V" for venting the interior of the container to atmosphere. Received within a reservoir-defining chamber 14e of housing 14 is the important stored energy means of this form of the invention, the purpose of which will presently be described.

First end 14a of the housing is closed by a fill and dispensing means for first permitting reservoir 14e to be filled with fluid via a reservoir inlet 15 (FIG. 2) by means of the reservoir fill assembly and then for dispensing fluid from the filled reservoir to the patient via a reservoir outlet. The fill and dispensing means here comprises a dispensing head assembly generally designated in the drawings by the numeral 18. As best seen in FIG. 2, assembly 18 includes a closure cap 20 which is receivable over container 14 to sealably close open end 14a thereof. Disposed within cap 20 is a flow control means for controlling the outward flow of fluid flowing from the reservoir or internal chamber 14e of container 14 toward the reservoir outlet. The flow control means of this embodiment of the invention comprises flow control elements including a generally annular shaped flow rate control element 24 and a generally annular shaped filter element 26. The flow control means further includes valve means which is supported within head assembly 18 by an apertured support 27 which also supports elements 24 and 26. A bore 20a is provided in the forward wall 20b of cap 20 (see FIG. 4) so as to closely receive therewithin a portion of the valve means. In a manner presently to be described, the valve means functions to control fluid flow between reservoir 14e and the fluid passageway 30a of a luer connector 30 which extends outwardly from wall 20b of cap 20. In the present form of the invention, a centrally disposed fluid passageway 30a defines the fluid inlet 15 of the device. As shown in FIGS. 1A and 2, the valve means here comprises a valve member 32 having a reduced diameter neck portion 32a and a seat engaging portion 32b which sealably engages a valve seat 34 formed internally of bore 20a.

Turning to FIG. 3, it is to be observed that bore 20a includes a plurality of circumferentially spaced bypass flow channels 35 which permit fluid flow into the reservoir of the device when valve member 32 is moved rearwardly away from seat 34. As seen in FIG. 2, cap 20 is also provided with an annular collector manifold 36 having micro-channels 38 that direct fluid flow from the reservoir of the device toward the reservoir outlet port 40 via a fluid passageway 41. Connected to outlet port 40 is a delivery conduit 42 preferably having at its outboard end a suitable connector such as a male luer fitting which can mate with an appropriate female luer cap.

Disposed within the reservoir 14e of the container 14 is the previously mentioned stored energy means of the invention, which functions to controllably urge fluid contained within the reservoir outwardly of the device via the flow control means. This unique stored energy means here comprises a specially configured elastomeric shaped article member 48 which is movable from a first, partially compressed configuration to a second, more compressed configuration wherein it has a tendency to return toward its first configuration. As best seen in FIG. 1A, article 48 comprises an elongated compressible member having a plurality of longitudinally spaced apart grooves and ridges 48a and 48b respectively. As indicated in FIG. 1A, the length "L+n" of member 48 is greater than the inside length "L" of container 14 so that upon assembly, member 48 will be precompressed by an amount proportional to the relative dimensions of "L+n" and "L". However, it is to be understood that in some instances member 48 may be substantially uncompressed in its starting configuration.

As discussed in U.S. Ser. No. 08/473,650, which is incorporated herein by reference, the stored energy means can be constructed from a wide variety of materials including rubbers, plastics and other thermoplastic elastomers (TPE) and thermoplastic urethane (TPU). By way of example, suitable materials include latex rubber, rubber polyolefins, polyisoprene (natural rubber), butyl rubber, nitrile rubber, polyurethane, vinyls, vinyl-end-blocked polydimethylsiloxanes, other homopolymer, copolymers (random alternating, block, graft, cross-link and star block), silicones and other flouropolymers, mechanical polyblends, polymer alloys and interpenetrating polymer networks.

In operating the apparatus of the present form of the invention, with the outlet conduit 42 suitably closed by a luer cap or the like, filling of the reservoir of the device with the fluid to be dispensed can readily be accomplished using the novel reservoir fill assembly of the invention, the character of which will now be described.

Turning particularly to FIGS. 4 and 5, the present form of the novel reservoir fill assembly 12 of the invention can be seen to comprise three major components, namely a container subassembly 156, an adapter subassembly 158, and an adapter or pusher sleeve 160. Container subassembly 156 includes a container such as a vial 157 which contains the medicinal fluid with which the reservoir of the dispensing apparatus is to be filled. Adapter subassembly 158 functions to interconnect the fill assembly with the medicament dispenser in a manner such that fluid can be transferred from container 157 to reservoir 14e of the dispenser component. As will presently be described, this fluid transfer is accomplished by urging sleeve 160 forwardly into the adapter subassembly and telescopically over container 157.

As best seen in FIG. 5, container 157 includes a fluid chamber 163 having first and second open ends 163a and 163b (FIG. 5). First open end 163a is sealably closed by closure means, here provided in the form of septum assembly 164 (FIG. 4), which includes a pierceable septum 164a and a clamping ring 164b. Septum 164a is pierceably by the cannula means or cannula 165 of the adapter subassembly 158. Cannula 165 is mounted centrally of an end wall 158a of body 158b of the adapter subassembly. As indicated in FIG. 4, septum assembly 164 is held securely in position within open end 163a of chamber 163 by the previously mentioned clamping ring 164b.

To expel fluid from fluid chamber 163 and into cannula 165 of the adapter subassembly and thence into reservoir 14e of the dispenser unit, a plunger 168 is telescopically movable within the chamber by pusher sleeve subassembly 160. To accomplish this movement, sleeve assembly 160 is provided with pusher means shown here as a pusher rod 176 which is integrally formed with end wall 160a of the sleeve (see also FIG. 6).

Referring particularly to FIGS. 5 and 7, it is to be noted that adapter subassembly 158 includes outer and inner, generally cylindrically shaped walls 158c and 158d which define therebetween an elongated annular space 158e within which sleeve component 160 is telescopically received. As shown in FIG. 4, container assembly 156 is closely receivable with a chamber 159 formed internally of wall 158d of the adapter subassembly and can be urged forwardly of chamber 159 by inward telescopic movement of sleeve 160 into space 158e. More particularly, as indicated in FIG. 5, the inboard end 176a of pusher rod 176 engages plunger 168 and urges it inwardly of reservoir 163 as sleeve 160 is moved inwardly of annular space 158e.

During the initial mating of sleeve 160 with adapter subassembly 158, the resistance of the fluid within vial 157 will resist movement of plunger 168 inwardly of reservoir 163 so as to cause the entire vial cartridge assembly 156 to initially move inwardly of chamber 159 to a position wherein septum 164a is engaged by cannula 165 of the adapter subassembly. A continued inward force on sleeve 160 will cause cannula 165 to pierce septum 164a in the manner shown in FIG. 4, thereby opening fluid communication between reservoir 163 of vial 157 and the internal fluid passageway 165a of cannula 165 (FIG. 5). Once septum 164a has been pierced, pusher rod 176 will urge plunger 168 forwardly of reservoir 163 from a first location proximate open end 163b to a second location proximate end 163a. As plunger 168 moves forwardly of reservoir 163, fluid within the reservoir will be caused to flow into cannula passageway 165a and toward a valve support assembly generally designated in the drawings by the numeral 180. Valve support assembly 180 is held in close proximity with wall 158a of adapter subassembly 158 by a cap-like member 182 which is connected to outer wall 158c by any suitable means such as by sonic welding. Cap-like member 182 also surrounds and protects an outwardly extending extension 180a of assembly 180 which includes a centrally disposed fluid passageway 180b. Disposed between cannula 165 and passageway 180b is a valve means shown here as an umbrella type check valve 183 for permitting fluid flow from cannula 165 toward passageway 180b of the valve operating extension, but blocking fluid flow in the opposite direction. As shown in FIG. 4 check valve 183, which is of conventional construction, is disposed within a chamber 180c formed within the reservoir fill assembly 12. The construction and operation of valve 183 is well understood by those skilled in the art.

Figure 12:
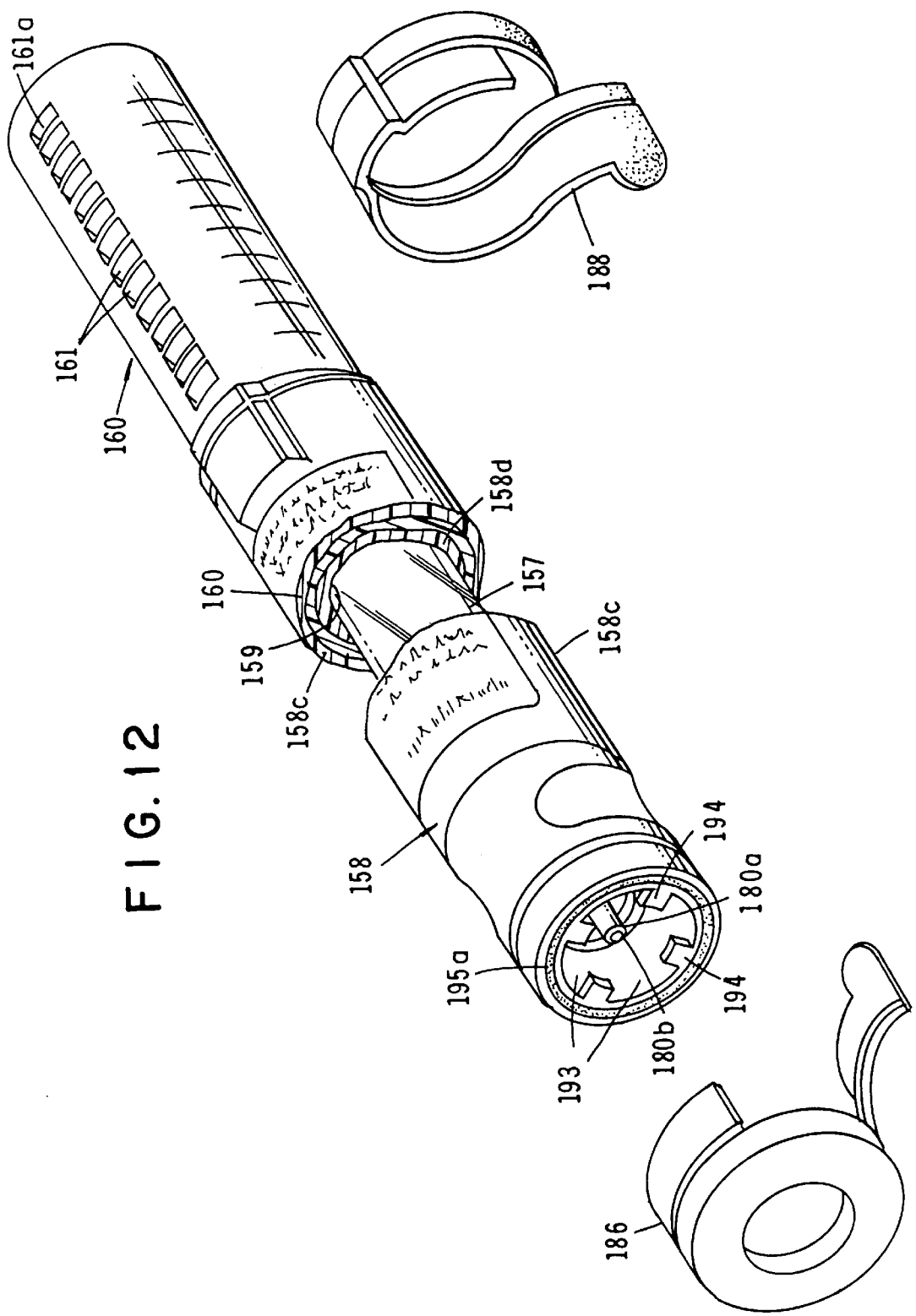
FIG. 12 is a generally perspective, partly exploded view of the reservoir fill assembly shown in FIG. 11 partly broken away to show internal construction.

Prior to use, the adapter subassembly 158 of the reservoir fill assembly 12 is maintained in a protected and substantially sterile configuration by tear-away end caps 186 and 188 (see FIG. 11). As indicated in FIGS. 1 and 12, tear-away end cap 186 is receivable over and closes the forward end of adapter subassembly 158, while tear-away end cap 188 is received over and closes the rearward open end portion of adapter subassembly 158. Similarly, as shown in FIG. 1, a tear-away cap 190 is received over and closes first end 163a of container subassembly 156. To close and protect the inlet 30b of the delivery device, a suitable, tight fitting enclosure cap 30c is provided (FIG. 1A). cap 30c is closely received over luer connector 30 and maintains the fluid inlet passageway of the device in a closed and sterile condition.

At the time of use of the apparatus of the invention, cap 188 is removed from the inboard end of adapter assembly 158 and cap 190 is removed from container or vial cartridge 156. This done, the first end of the vial can be inserted into chamber 159 of adapter subassembly 158 in the manner shown in FIG. 12. With the vial cartridge assembly inserted into chamber 159, sleeve 160 is then mated with adapter assembly 158 in the manner shown in FIG. 12 by inserting the leading edge of the pusher sleeve into annular space 158e. A forward movement of the pusher sleeve into annular space 158e will cause pusher rod 176 to move into pressural engagement with plunger 168. As previously mentioned, the fluid within chamber 159 of the vial assembly will resist inward movement of plunger 168 causing the entire vial assembly to move forwardly within chamber 158d to the position shown in FIG. 13 where cannula 165 of the adapter subassembly interengages pierceable septum 164a of the container assembly. A continued inward force on the pusher sleeve 160 will cause hollow cannula 165 to pierce septum 164a thereby opening fluid communication between chamber 163 of vial 157 and passageway 180b of valve support assembly 180.

With the components in the configuration shown in FIG. 12, closure cap 30c is removed from luer connector 30 of the medicament dispenser 10 and cap 186 is removed from the forward end of adapter subassembly 158. This done, the adapter assembly 158 can be mated with the dispenser apparatus in the manner shown in FIG. 14 and lockably interconnected therewith by connector means which here comprises a bayonet type connector arrangement of the character best seen in FIGS. 1, 1A, and 13. More particularly, as there shown, the dispensing head assembly 18 of the dispenser unit is provided with a dispenser connector comprising a plurality of circumferentially spaced-apart locking ears 190. Similarly, cap 182 of the adapter subassembly 158 is provided with an adapter connector comprising a plurality of circumferentially spaced apart slots 193 (FIGS. 10 and 12) which are adapted to receive locking ears 190. With this construction, after locking ears 190 have been received within slots 193, rotation of adapter subassembly 158 relative to the dispensing means will, bring ears 190 into locking engagement with circumferentially spaced tabs 194 provided on cap 182 of the adapter subassembly, which tabs comprise a part of the adapter connector of the invention (see FIG. 14). To enable smooth rotation of the adapter subassembly relative to the dispenser unit, an antilock elastomeric ring 195 is formed on the front face of cap 20 (FIG. 2). Similarly, an antilock ring 195a is formed on cap 182 of the adapter subassembly (FIGS. 4 and 5).

During mating of the adapter subassembly with the dispenser unit 10, extension 180a of the member 180 which functions as a valve operating means for moving valve 32 away from seat 34, will be closely received into the inlet port of luer fitting 30 in the manner shown in FIG. 14. During mating, an elastomer ring 180d (FIG. 14A) will sealably engage the inner wall of the luer connector to form a substantially leak-tight seal. To enhance this seal, the inner wall of the luer connector is covered with an elastomeric designated as 30c (FIG. 14A). As the extension 180a seats, valve member 32 will be moved away from seat 34 in the manner shown in FIG. 14A. It is to be understood that, in some instances, covering 30c can be eliminated and ring 180*d* can be relied upon for sealing. Similarly 180*d* can be eliminated in favor of covering 30*c*.

With adapter subassembly 158 suitably mated with the dispenser apparatus 10 in the manner shown in FIG. 14, the exertion of inward pressure on pusher sleeve 160 will cause plunger 168 to move forwardly of vial chamber 163 in the manner shown in FIG. 14 causing the fluid contained within chamber 163 to flow into hollow cannula 165 and past check valve 183 in chamber 180*c* of valve supporting assembly 180. The fluid will then flow into passageway 180*b* and radial passageways 180*e* of extension 180*a*. Because valve member 32 of the dispenser apparatus has been moved away from seat 34 by extension 180*a*, fluid will flow into bypass flow channels 35 formed in bore 20*a* of cap 20. The fluid under pressure will next flow into chamber 14*e* in the direction of arrow 30*e* of FIG. 14 via inlet opening 30*d*. As the fluid under pressure flows into chamber 14*e* of the dispensing apparatus, the stored energy means, or member or article 48, will be further compressed causing additional internal stresses to be built up within the member, which stresses tend to return the member toward its first configuration. With reservoir 14*e* thusly filled, valve member 32 will once again move into seating engagement with valve seat 34 (FIG. 13A) thereby preventing fluid flow in a direction toward the adapter assembly (see also FIG. 14).

Turning particularly to FIGS. 4 and 5, it is to be noted that pusher sleeve 160 is provided with a plurality of longitudinally spaced, upstanding teeth 161 which forms a part of the locking means of the invention for locking sleeve 160 to the adapter assembly after filling of reservoir 14*e*. As sleeve 160 is inserted into annular space 158*e*, teeth 161 will slide under an inwardly extending tab 165*a* provided in a locking clip 165 which also forms a part of the locking means and which is carried within a relief 158*f* formed in housing 158*c* in the manner shown in FIGS. 4 and 5 (see also FIGS. 7 and 8). When sleeve 160 is fully inserted into annular space 158*e* as shown in FIG. 4, tab 165*a* will lockably engage rearward most tooth 161*a* preventing withdrawal of the sleeve from space 158*e*.

Following the filling step, the adapter assembly 158 can be disconnected from the dispenser unit 10 and the closure cap 30*c* once again placed over luer fitting 30 to maintain the fitting in the protected substantially sterile configuration. At any time after the reservoir filling step, the fluids contained within reservoir 14*e* can be delivered to the patient by affixing the dispenser unit to the patient using the patient interconnection means or wings 200 which are placed in engagement with the patient's limbs such as an arm or leg and then taped or otherwise suitably affixed in position. With the unit affixed to the patient, opening of delivery conduit 42, will permit the stored energy means or member 48 to move toward its first configuration thereby controllably urging fluid flow outwardly of the device via apertures 27*b* in support 27 and via filter and rate control elements 24 and 26. Fluid flowing through these elements will flow into annular shaped fluid collection passageway 36 and then outwardly of the device via passageway 40 and delivery tube 42. Filter 26 which functions to filter particulate matter from the fluid flowing outwardly of the reservoir 14*e* is of a character well known to those skilled in the art and can be constructed from various readily available materials such as polysolfone and polypropylene wafers having a desired porosity. Similarly, rate control element 24 can be constructed from any suitable porous material such as polycarbonate, a polyether, ether ketone (PEEK) a metal or a sintered ceramic having the desired porosity.

As previously mentioned, various fluids can be dispensed from container 14 including, by way of example, beneficial as medicaments of various types, drugs, pharmaceuticals, hormones, antibodies, biologically active materials, elements, chemical compounds, or any other suitable materials used in diagnostic cures medication, treatment, or preventing of diseases, or maintenance of the good health of the patient.

Turning to FIG. 15, the forward portion of an alternate form of medicament dispenser 10 is there shown. This form of the invention is similar in most respects to that shown in FIGS. 1 through 14 and like numbers are used to identify like components. The principal difference between the apparatus shown in FIG. 15 and the previously described embodiments resides in the provision of a different fluid flow control means which here comprises a porous element 203 which is disposed between reservoir 14*e* and outlet passageway 40. Element 203 comprises a microporous metal such as stainless steel. The element can also be constructed from a porous ceramic or porous plastic material. The specific kinds and type of material requirements of elements 203 are based on agent compatibility, required inertness, stability and safety.

Figure 16:
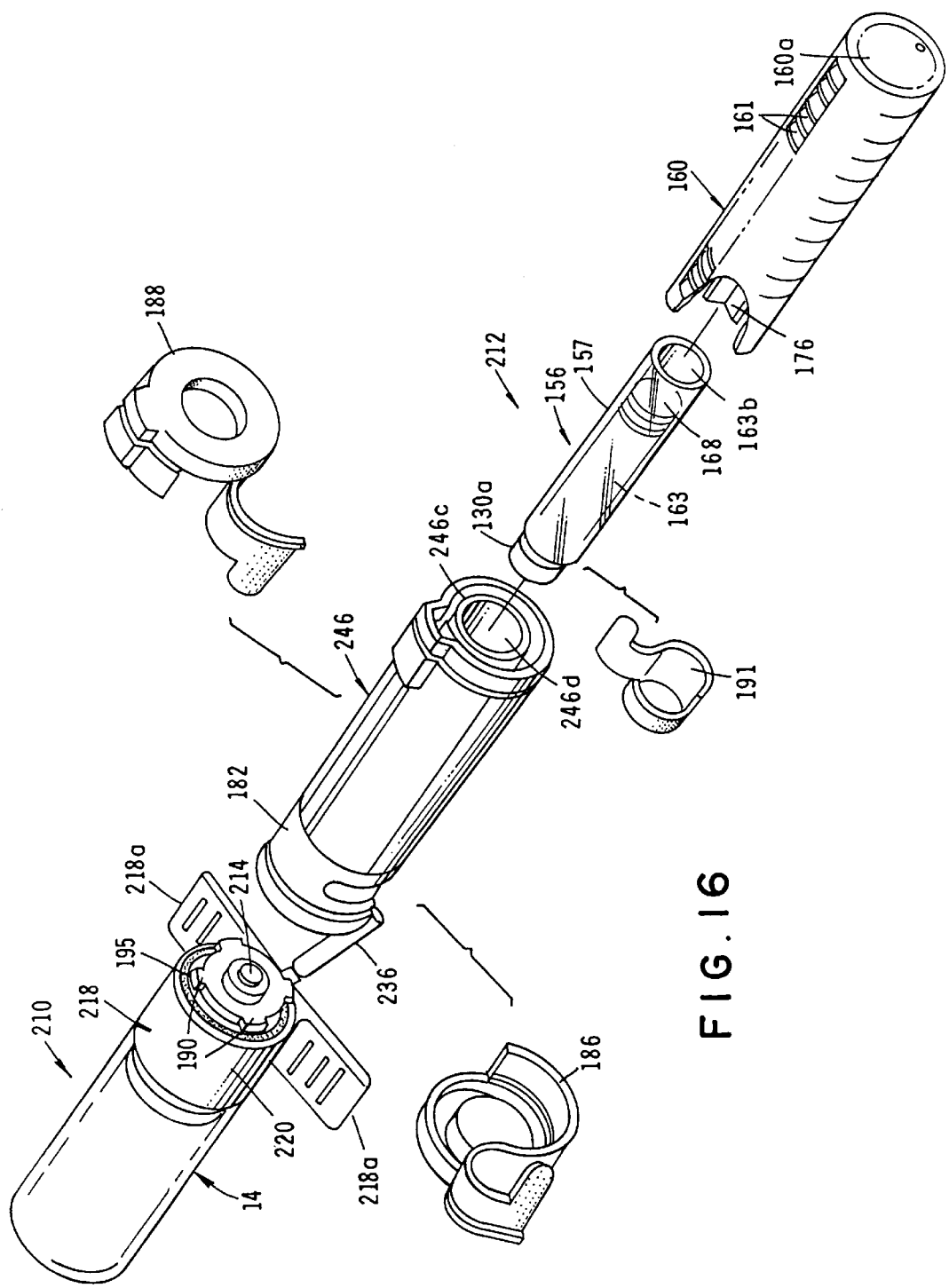
FIG. 16 is a generally perspective, exploded view of an alternate form of the fluid dispensing apparatus and reservoir fill assembly of the present invention.

Referring next to FIGS. 16 through 22, an alternate embodiment of the dispensing apparatus of the invention is there shown. As before, the apparatus comprises a fluid dispenser and a cooperating reservoir fill assembly. This alternate embodiment is similar in many respects to that shown in FIGS. 1 through 12 and like numbers are used to identify like components. In FIG. 16, the fluid dispenser of this alternate embodiment is shown fully assembled and is generally designated by the numeral 210 while the reservoir fill assembly is shown in exploded form and is generally designated by the numeral 212.

The major difference between the apparatus of this latest form of the invention and that shown in FIGS. 1 through 12 resides in the fact that the medicament dispenser 210 is provided with a pierceable septum 214 (FIG. 17), which is used to fill the reservoir of the device rather than the luer connector 30 and valve 32 shown in FIG. 1A. Accordingly, to enable mating of the reservoir fill assembly with the dispenser unit, the reservoir fill assembly includes a piercing cannula 250 (FIG. 20), which takes the place of the valve means shown in FIG. 5.

Once again, the medicament dispenser 210 is of the same general character as shown in FIGS. 6, 7, and 8 of U.S. Ser. No. 08/473,650 which application is incorporated herein by reference.

As best seen in FIGS. 17, 18 and 19, the medicament dispenser 210 of this latest form of the invention comprises a housing assembly including a housing 14, which is of identical construction to that previously described herein. Received within a reservoir-defining chamber 14*e* of housing 14 is the stored energy means which is also somewhat similar to that previously described herein. As before, the first end 14*a* of the container is closed by a fill and dispensing means for first permitting chamber 14*e* to be filled with fluid by means of the reservoir fill assembly and then for dispensing fluid from the filled reservoir to the patient. The fill and dispensing means here comprises a dispensing head assembly generally designated in the drawings by the numeral 218. As best seen in FIG. 17, assembly 218 includes a closure cap 220 which is receivable over housing 14 to close open end 14*a* thereof. Disposed within cap 220 is a flow control means for controlling the flow of fluid into and out of the reservoir or internal chamber 14*e* of housing 14. The flow control means of this latest embodiment of the invention is slightly different from that previously described herein and comprises the previously described septum 214 as well as a generally annular shaped flow rate control element 224 and a generally annular shaped filter element 226. The flow control means further includes support member 228 which is disposed between, and provides support to, rate control element 224 and filter element 226. As shown in FIG. 17, support member 228 is provided with a plurality of circumferentially spaced fluid flow passageways 228a.

As shown in FIG. 18, cap 220 is provided with an annular shaped fluid collection channel 230 which is in communication with a passageway 231 and also with the outlet port 232 of the apparatus. Connected to cap 220 proximate the outlet port 232 is a hollow infusion needle 234 which is protectively surrounded by a integrally molded twist off cap 236 and a closely fitting closure sleeve 238, which cooperate to maintain the needle in a protected, substantially sterile condition and prevent fluid flow therethrough until time of use.

Disposed within chamber 14e of the container is the alternate form of stored energy means of the invention, which functions to urge fluid contained within reservoir 14e outwardly of the device via the flow control means and infusion needle 234. This unique stored energy means here comprises a cellular mass such as the specially configured sponge like member 240 which is movable from a first configuration to a second, more compressed configuration wherein it has a tendency to return toward its first configuration. Member 240 can comprise either an open cell or closed cell sponge of appropriate resilient material. The stored energy means, or member 240 can be constructed from a wide variety of materials of the type discussed in Ser. No. 08/473,650, including rubbers, plastics and other thermoplastic elastomers (TPE) and thermoplastic urethane (TPU).

In operating the apparatus of the form of the invention shown in FIGS. 16 through 22, with the fluid passageway of needle 234 closed by closure sleeve 238, reservoir 14e is filled with the fluid to be dispensed using the novel reservoir fill assembly 212, the details of construction of which will presently be described.

As the fluid under pressure flowing from the reservoir fill assembly 212 enters reservoir 14e, it will engage a piston-like member 244 which is telescopically movable longitudinally of reservoir 14e. This fluid under pressure will urge member 244 telescopically inward of the reservoir causing the stored energy member to be compressed.

Upon removing twist off cap 236 and closure sleeve 238 from the needle thereby opening the fluid delivery path of the device, stored energy member 240 will tend to return toward its starting configuration and, in so doing, will controllably urge fluid flow outwardly of reservoir 14e via filter element 226 and rate control element 224. Fluid flowing through these elements will next flow into annular shaped fluid passageway 230 and then outwardly of the device through infusion needle 234. Filter 226, which functions to filter particulate matter from the fluid flowing outwardly from reservoir 14e is of the character previously described herein as is rate control element 224. As before, the various fluids previously identified herein can be dispensed from reservoir 14e.

During the delivery step, the infusion needle 234 is, of course, inserted into the vein of the patient. To stabilize the device, cap assembly 218 includes patient interconnection means which here comprise curved, wing-like base portions 218a which can be used to affix the device to the patient using an adhesive pad assembly 218b which is connected to the lower surfaces of the wings 218a.

Turning particularly to FIGS. 16 and 20, the novel reservoir fill assembly 212 of this latest form of the invention can be seen to once again comprise three major components, namely a container subassembly 156 which is identical to that previously described, an adapter subassembly 246 which is of slightly different construction from that previously described, and an adapter or pusher sleeve 160 which is identical to that previously described. As before, container subassembly 156 includes a container such as a vial 157 which contains the medicinal fluid with which the reservoir of the dispensing apparatus is to be filled. As before, adapter subassembly 246 functions to interconnect the reservoir fill assembly with the dispensing apparatus in a manner such that fluid can be transferred from container 157 to reservoir 14e of the dispenser component. This fluid transfer is accomplished in the manner earlier described by urging sleeve 160 forwardly into the adapter subassembly and telescopically over container 157.

More particularly, to expel fluid from fluid chamber 163 of container 157 and into reservoir 14e of the dispenser unit via the adapter subassembly 246, a plunger 168 is telescopically movable within the chamber by pusher sleeve subassembly 160 which includes the previously described pusher means or pusher rod 176 which, as before, is integrally formed with end wall of the sleeve.

Referring particularly to FIGS. 20 and 21, it is to be noted that adapter subassembly 246 of this last embodiment of the invention includes inner and outer, generally cylindrically shaped walls 246a and 246b which define therebetween an elongated annular space 246c within which sleeve component 160 is telescopically received. As before, container assembly 156 is closely receivable within a chamber 246d formed internally of wall 246a of the adapter subassembly and can be urged forwardly of chamber 246d in the same manner previously described by inward telescopic movement of sleeve 160 into space 246c. The continued exertion of an inward force on sleeve 160 will cause cannula 165 of the adapter subassembly 246 to pierce septum 164a of the container subassembly in the manner shown in FIG. 21. This action opens fluid communication between reservoir 163 of vial 157 and the internal fluid passageway 165a of cannula 165. Once septum 164a has been pierced, pusher rod 176 will urge plunger 168 forwardly of reservoir 163 from a first location proximate open end 163b to a second location proximate end 163a. As plunger 168 moves forwardly of reservoir 163, fluid within the reservoir will be caused to flow into cannula passageway 165a for delivery toward reservoir 14e of the dispensing apparatus.

As best seen in FIG. 20, a second piercing cannula 250 is held in position within the adapter subassembly 246 by a cannula support 252 which is, in turn, held in close proximity with the end wall 246e of adapter subassembly 246 by cap-like member 182 which is identical to that previously described and which can be connected to outer wall 246b by any suitable means such as by sonic welding. Cap-like member 182 surrounds and protects the outboard end 250a of hollow, piercing cannula 250.

Disposed between second piercing cannula 250 and piercing cannula 165 is a valve means shown here as the previously described umbrella check valve 183 which here functions to control fluid flow from internally passageway 165a of cannula 165 into the internal passageway of second piercing cannula 250. As before, check valve 183 is disposed within a chamber 252a formed within the body 252b of cannula support 252.

As was the case with the embodiment of the invention shown in FIGS. 1 through 15, prior to use, the adapter subassembly 246 of the reservoir fill assembly 210 is maintained in a protected and sterile configuration by tear-away end caps 186 and 188 (see FIG. 16). Similarly, a tear-away cap 190 is received over and closes first end 163a of container subassembly 156.

At the time of use of the apparatus of this alternate form of the invention, caps 186 and 188 are first removed from the ends of adapter assembly 246. This done, the adapter subassembly 246 can be mated with the dispenser unit 210 and lockably interconnected therewith in the manner previously described by locking means which are identical to those described in connection with the first embodiment of the invention. However, in this latest embodiment of the invention, as adapter assembly 246 is moved into mating engagement with the dispenser unit 210, in the manner shown in FIGS. 20 and 21, hollow cannula 250 will pierceably engage septum 214 of the dispenser unit. As indicated in FIG. 21, once cannula 250 pierces septum 214, chamber 14e of the dispenser unit is placed in fluid communication with fluid passageway 165a of hollow cannula 165 of adapter assembly 246.

As illustrated in FIG. 20, prior to mating the adapter subassembly 246 with the dispenser apparatus 210, cap 190 has been removed from container or vial 157 so that the first end of the vial cartridge can be inserted into chamber 246d of adapter subassembly 246. After the vial cartridge assembly has been inserted into chamber 246d, sleeve 160 is then mated with adapter assembly 246 in the manner previously described by inserting the leading edge of the pusher sleeve into annular space 246c. A forward movement of the pusher sleeve will cause pusher rod 176 to move into pressural engagement with plunger 168. As previously mentioned, the fluid within chamber 163 of the vial assembly will resist inward movement of plunger 168 causing the entire vial assembly to move forwardly within chamber 246d to a position where cannula 165a of the adapter subassembly interengages pierceable septum 164a of the container assembly. A continued inward force on the pusher sleeve 160 will cause hollow cannula 165 to pierce septum 164a in the manner shown in FIG. 21 thereby opening fluid communication between chamber 163 of vial 157 and chamber 14e of the dispensing apparatus 210. Continued inward pressure on pusher sleeve 180 will cause filling of reservoir 14e in the manner shown in FIG. 21. As there shown, plunger 168 has moved forwardly of vial chamber 163 thereby causing the fluid contained within chamber 163 to flow into hollow cannula 165, past check valve 183, into hollow cannula 250 and then into chamber 14e. As the fluid under pressure flows into chamber 14e of the dispensing apparatus the stored energy means or sponge-like member 240, will be compressed in a manner to cause internal stressed to be built up within the member which stresses tend to return the member toward its unstressed configuration.

Following the filling step and removal of the adapter assembly from the dispensing unit, the apparatus is in condition to infuse medicinal fluids into the patient. This infusion step is accomplished by first removing the cannula cover 236 and plug 238 to expose the infusion cannula or needle 234. Following insertion of the needle into the patient, the dispensing apparatus can be affixed to the patient using the patient interconnection means or wing-like base members 218a which extend outwardly from cap 218. The adhesive pad 218b which is affixed to the wing members is placed in engagement with the patient's limbs such as an arm or leg so as to hold the dispensing apparatus securely in position. During the infusion step, the stored energy means 240 will tend to return toward its starting configuration urging member 244 forwardly of reservoir 14e thereby controllably urging fluid flow outwardly of the device via the filter and rate control elements 226 and 224. Fluid flowing through these elements will flow into annular shaped fluid collection passageway 230 and then outwardly of the device via infusion cannula 234. When all of the medicinal fluids have been expelled from reservoir 14e, member 244 will be in the final forward position shown in FIG. 20.

Turning next to FIGS. 22 and 22A, the forward portion of an alternate form of dispenser 210 is there shown. This form of the invention is similar in most respects to that shown in Figures through 21 and like numbers are used to identify like components. The principal difference between the apparatus shown in FIGS. 7 and 22A and the previously described embodiments resides in the provision of a different fluid flow control means which here comprises porous elements 203a which is disposed between reservoir 14e and passageway 23 of member 220. Element 203a is similar to previously described element 203, but uniquely comprises a pressed, microporous plastic element constructed from a polyether ether ketone (PEEK) material. Such processed material is commercially available from Upchurch Scientific, Inc. of Seattle, Wash. and is more fully described in U.S. Pat. No. 5,651,931.

Referring to FIG. 22B, an alternate form of rate control assemblage is there shown. This unique assemblage is receivable within a cavity 205 (FIG. 22A), and comprises a plastic base 207a, a thin flow control wafer 207b superimposed over base 207a and a thin filter member 207c superimposed over wafer 207b. Wafer 207b includes an extremely small laser drilled aperture or microbore "MB".

Plastic base 207a can be constructed from any suitable plastic material including polycarbonate acrylic, polypropylene and the like. Wafer 207b is preferably constructed from a film material such as polyester which can be eximer laser drilled to form one or more microbores "MB". This drilling technique is such that sharp edge microbores of between about one micron and about 50 microns in diameter or layer can be formed to permit precisely controlled ultraslow fluid flow. Filter 207c can be constructed from various porous materials including those materials earlier described in connection with filter member 26. Elements 207a, 207b, and 207c can be joined together at their peripheries by various means including adhesive and thermal bonding.

Turning to FIGS. 23 through 26, still another embodiment of the dispensing apparatus of the invention is there shown. As before, the apparatus comprises a fluid dispenser and a cooperating reservoir fill assembly. This alternate embodiment is similar in most respects to that shown in FIGS. 16 through 22 and like numbers are used to identify like components. The major difference between the apparatus of this latest form of the invention and that shown in FIGS. 16 through 22 resides in the fact that the dispenser unit is provided with a slit septum 261 while the reservoir fill assembly is provided with a blunt end cannula 263 which is adapted to penetrate slit septum 261. Save for this difference, this latest form of the invention operates in the same fashion as the embodiment of FIGS. 16 through 22.

Figure 27:
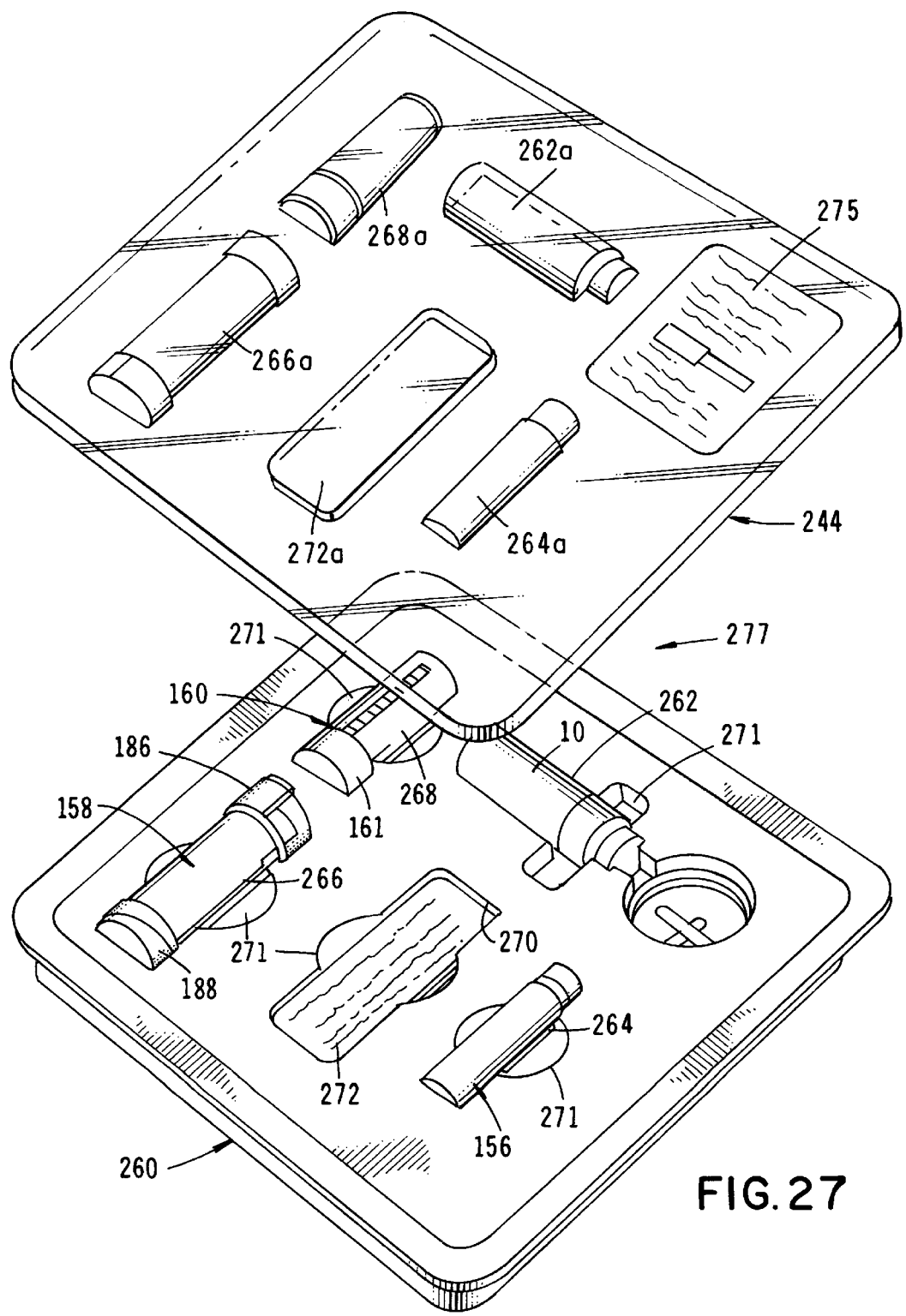
FIG. 27 is a generally perspective, exploded view of one form of the transport means of the invention for the storage and transport of the various components which make up the dispenser apparatus and cooperating reservoir fill assembly.

Referring next to FIG. 27, the novel transport apparatus of the present invention is there shown for conveniently packaging and transporting the apparatus of the invention as described in the preceding paragraphs. This novel transport apparatus comprises a molded base unit 260 which includes a plurality of spaced-apart component receiving cavities for closely receiving the various components of the apparatus of the invention. More particularly, the cavity designated in FIG. 23 by the numeral 262 is adapted to receive either of the dispensing apparatus 10 or 210. In FIG. 23, dispensing apparatus 10 is shown received within cavity 262, but the cavity will also support and protect the alternate form of the dispensing unit 210.

The second cavity 264 is provided in base 260 for supporting the fluid container or vial assembly 156 of the apparatus. A cavity 266 is also provided in base 260 for supporting either form of the adapter assembly of the invention, that is, either adapter assembly 158 or, alternatively, adapter assembly 246. In FIG. 23, adapter assembly 158 is shown in position within cavity 266. As previously mentioned during storage and transport of the apparatus of the invention, closure caps 186 and 188 are in position over the ends of the adapter unit. Finally, a cavity 268 is provided for supporting the pusher sleeve component 160 of the apparatus of the invention. In the form of the invention shown in FIG. 23, the open end of the pusher sleeve 160 is shown closed by a removable cap 161. Also formed within base 260 is a use instruction cavity 270 which adapted to house the detailed printed use instructions 272 which set forth in detail the manner in which the apparatus of the invention is to be used and can also contain suitable information identifying the liquid medicament contained within vial 156. Disposed transversely of each of the component receiving cavities 262, 264, 266, 268 and 270 is finger receiving channel 271 for use in conveniently removing the component from its component receiving cavity.

Fitted over and interconnected with base 260 is a clear plastic, vacuum formed cover 274. As shown in FIG. 23, cover 274 is provided with cavities which are indexable with the cavities formed in base 262 and are configured to receive the various components of the apparatus disposed within the cavities formed in base 262. More particularly, cover 274 is provided with a first cavity 262a which receives the upper portion of the dispenser apparatus of the invention. Similarly, cover 274 is provided with cavities 264a, 264a, and 264a which are adapted to receive the upper portions of respectfully vial assembly 156, adapter assembly 158 and sleeve assembly 160 respectively. Similarly, a cavity 272a houses a portion of the care and use instructions 272.

When cover 274 is emplaced over base 260 and suitably connected thereto, the various components of the apparatus of the invention are readily visible through the cover 274 and following appropriate sterilization, are maintained in a protected, substantially sterile environment during transport and storage of the apparatus of the invention to the user. Suitable labeling 275 describing the apparatus can be affixed to the upper surface of cover 274 in the manner shown in FIG. 23. With various components of the apparatus sealably housed within the packaging and transport unit 277, the apparatus can be safely and conveniently aseptically stored either in the hospital or in the home care facility until time of use.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A dispensing apparatus for dispensing fluid comprising:
   (a) a fluid dispenser comprising:
   (i) a housing assembly including a housing having a fluid reservoir, said reservoir having a fluid inlet for filling said reservoir with fluid and a fluid outlet for permitting fluid flow from said fluid reservoir, said housing assembly having a dispenser connector; and
   (ii) stored energy means for acting upon the fluid contained within said reservoir to cause the fluid to controllably flow through said outlet, said stored energy means comprising a compressively deformable, elastomeric member carried within said reservoir, said elastomeric member being expandable to cause fluid flow from said reservoir toward said fluid outlet; and
   (b) a reservoir fill assembly for filling said reservoir with the fluid to be dispensed, said reservoir fill assembly comprising:
   (i) a container subassembly including a container having a body portion, a fluid chamber, and first and second open ends; closure means for sealably closing said first open end of said container; and a plunger telescopically movable within said container from a first location proximate said second open end to a second, spaced-apart location;
   (ii) an adapter subassembly comprising a hollow housing having an annular passageway and a first open end for telescopically receiving a part of said body portion of said container of said container subassembly and a second end, said hollow housing further including an adapter connector mateably interconnectable with said dispenser connector for removably interconnecting said adapter subassembly with said fluid dispenser; and
   (iii) an adapter sleeve telescopically receivable with said annular passageway said sleeve subassembly including pusher means for engagement with said plunger to move said plunger within said container between said first and second locations.

2. An apparatus as defined in claim 1 in which said housing assembly further includes a dispensing head assembly connected to said housing, said dispenser connector being formed on said dispensing head assembly.

3. An apparatus as defined in claim 1 in which said elastomeric member comprises a flexible, resilient, polymeric member.

4. An apparatus as defined in claim 1 in which said elastomeric member comprises a cellular mass.

5. An apparatus as defined in claim 1 further including locking means for lockably interconnecting together said adapter sleeve and said adapter subassembly.

6. An apparatus as defined in claim 1 in which said fluid dispenser further includes flow control means disposed between said reservoir and said fluid outlet for controlling fluid flow from said reservoir.

7. An apparatus as defined in claim 6 in which said flow control means comprises fluid flow rate control means for controlling the rate of the fluid flow from said reservoir toward said fluid outlet.

8. An apparatus as defined in claim 6 in which said flow control means comprises filter means for filtering particulate matter from fluid flowing from said reservoir.

9. An apparatus as defined in claim 6 in which said flow control means comprises a filter means for filtering fluid flowing from said reservoir and a cooperating rate control member for controlling the rate of fluid flow from said reservoir.

10. A dispensing apparatus for dispensing fluid comprising:

(a) a fluid dispenser comprising:
  (i) a housing assembly including:
    a. a housing having a fluid reservoir, said reservoir having a fluid inlet for filling said reservoir with fluid and a fluid outlet for permitting fluid flow from said fluid reservoir;
    b. a fill and dispensing means connected to said housing for filing said fluid reservoir and for dispensing fluid therefrom, said fill and dispensing means comprising a dispensing head assembly including a dispensing head and a flow control means carried by said dispensing head for controlling fluid flow into and out of said reservoir and a dispenser connector formed on said dispensing head assembly; and
  (ii) stored energy means for acting upon the fluid contained within said reservoir to cause the fluid to controllably flow through said outlet, said stored energy means comprising a compressively deformable, resilient member carried within said reservoir, said resilient member being expandable to cause fluid flow from said reservoir toward said fluid outlet; and
(b) a reservoir fill assembly for filling said reservoir with the fluid to be dispensed, said reservoir fill assembly comprising:
  (i) a container having a fluid chamber, closure means for sealably closing said fluid chamber, and a plunger telescopically movable within said fluid chamber from a first location to a second, spaced-apart location;
  (ii) an adapter subassembly comprising a hollow housing having an annular passageway and a first open end for telescopically receiving a part of said body portion of said container of said reservoir fill assembly and a second end, said hollow housing further including an adapter connector mateably interconnectable with said dispenser connector for removably interconnecting said adapter subassembly with said fluid dispenser; and
  (iii) an adapter sleeve telescopically receivable with said annular passageway said sleeve subassembly including pusher means for engagement with said plunger to move said plunger within said container between said first and second locations.

11. An apparatus as defined in claim 10 in which said flow control means further comprises valve means carried by said dispensing head for controlling fluid flow into said reservoir.

12. An apparatus as defined in claim 10 in which said flow control means further comprises a pierceable septum carried by said dispensing head for controlling fluid flow into said reservoir.

13. An apparatus as defined in claim 10 in which said flow control means comprises flow control elements disposed between said reservoir and said fluid outlet for controlling fluid flow from said reservoir.

14. An apparatus as defined in claim 13 in which said flow control elements include a fluid flow rate control means for controlling the rate of the fluid flow from said reservoir toward said fluid outlet.

15. An apparatus as defined in claim 13 in which said flow control elements include a filter means for filtering particulate matter from fluid flowing from said reservoir.

16. An apparatus as defined in claim 13 in which said elastomeric member comprises a flexible polymeric member.

17. An apparatus as defined in claim 13 in which said elastomeric member comprises a polymeric cellular mass.

18. An apparatus as defined in claim 13 further including locking means for lockably interconnecting together said adapter sleeve and said adapter subassembly.

19. An apparatus as defined in claim 18 in which said locking means comprise a plurality of upstanding teeth formed on said adapter sleeve.

20. A dispensing apparatus for dispensing fluid comprising:
(a) a fluid dispenser comprising:
  (i) a housing assembly including:
    a. a housing having a fluid reservoir, said reservoir having a fluid inlet for filling said reservoir with fluid and a fluid outlet for permitting fluid flow from said fluid reservoir;
    b. a fill and dispensing means connected to said housing for filing said fluid reservoir and for dispensing fluid therefrom, said fill and dispensing means comprising a dispensing head assembly including a dispensing head and a flow control means carried by said dispensing head for controlling fluid flow into and out of said reservoir and a dispenser connector formed on said dispensing head assembly said dispenser connector comprising a plurality of spaced apart locking ears; and
  (ii) stored energy means for acting upon the fluid contained within said reservoir to cause the fluid to controllably flow through said outlet, said stored energy means comprising a compressively deformable, elastomeric, polymeric member carried within said reservoir, said elastomeric, polymeric member being expandable to cause fluid flow from said reservoir toward said fluid outlet; and
(b) a reservoir fill assembly for filling said reservoir with the fluid to be dispensed, said reservoir fill assembly comprising:
  (i) a container subassembly including a container having a fluid chamber, a pierceable septum sealably closing said fluid chamber, and a plunger telescopically movable within said fluid chamber from a first location to a second, spaced-apart location;
  (ii) an adapter subassembly comprising:
    a. a hollow housing having an annular passageway and an internal chamber having a first open end for telescopically receiving a part of said body portion of said container of said reservoir fill assembly and a second end;
    b. a hollow cannula connected to said second end of said housing and extending into said internal chamber for piercing engagement with said pierceable septum of said container subassembly;
    c. a cap connected to said housing proximate said second end, said cap having an adapter connector mateably interconnectable with said dispenser connector, said adapter connector comprising a plurality of spaced apart tabs engagable with said locking ears; and
  (iii) an adapter sleeve telescopically receivable within said annular passageway, said sleeve subassembly including pusher means for engagement with said plunger to move said plunger within said container between said first and second locations.

21. An apparatus as defined in claim 20 in which said flow control means further comprises a pierceable septum carried by said dispensing head for controlling fluid flow into said reservoir.

22. An apparatus as defined in claim 20 in which said flow control means further comprises valve means carried by said dispensing head for controlling fluid flow into said reservoir.

23. An apparatus as defined in claim 22 in which said dispensing head assembly includes a central bore defining a valve seat and in which said valve means comprises a valve member movable within said bore toward and away from said valve seat.

24. An apparatus as defined in claim 23 in which said dispensing head assembly includes a luer connector and an outlet conduit in communication with said fluid outlet of said reservoir.

25. An apparatus as defined in claim 23 in which said reservoir fill assembly includes valve operating means for moving said valve member away from said valve seat.

26. A dispensing apparatus for dispensing fluid comprising:
(a) a fluid dispenser comprising:
(i) a housing assembly including a housing having a fluid reservoir, said reservoir having a fluid inlet for filling said reservoir with fluid and a fluid outlet for permitting fluid flow from said fluid reservoir, said housing assembly having a dispenser connector; and
(ii) stored energy means for acting upon the fluid contained within said reservoir to cause the fluid to controllably flow through said outlet, said stored energy means comprising a compressively deformable, elastomeric member carried within said reservoir, said elastomeric member being expandable to cause fluid flow from said reservoir toward said fluid outlet; and
(iii) flow control means disposed between said reservoir and said fluid outlet for controlling fluid flow from said reservoir;
(iv) an adapter subassembly comprising a hollow housing having an annular passageway and a first open end for telescopically receiving a part of said body portion of said container of said container subassembly and a second end, said hollow housing further including an adapter connector mateably interconnectable with said dispenser connector for removably interconnecting said adapter subassembly with said fluid dispenser; and
(v) an adapter sleeve telescopically receivable with said annular passageway said sleeve subassembly including pusher means for engagement with said plunger to move said plunger within said container between said first and second locations.

27. An apparatus as defined in claim 26 in which said flow control means comprises filter means for filtering particulate matter from fluid flowing from said reservoir.

28. An apparatus as defined in claim 26 in which said flow control means comprises fluid flow rate control means for controlling the rate of fluid flow from said reservoir toward said fluid outlet.

29. An apparatus as defined in claim 28 in which said fluid flow rate control means comprises a wafer having at least one microbore formed therethrough.

30. An apparatus as defined in claim 29 in which said wafer comprises a plastic film.

31. An apparatus as defined in claim 29 in which said wafer comprises polyester.

32. An apparatus as defined in claim 29 in which said microbore has a diameter between about one micron and about 50 microns.

33. An apparatus as defined in claim 29 in which said microbore has at least one sharp edge.

* * * * *